US012624127B2

(12) United States Patent
Chan et al.

(10) Patent No.: US 12,624,127 B2
(45) Date of Patent: May 12, 2026

(54) CHITOSAN DERIVATIVES AS ANTIMICROBIALS AND SYNERGISTIC COMBINATIONS THEREOF

(71) Applicant: Nanyang Technological University, Singapore (SG)

(72) Inventors: Bee Eng Mary Chan, Singapore (SG); Zhangyong Si, Singapore (SG); Zheng Hou, Singapore (SG); Yogesh Shankar Vikhe, Singapore (SG); Kishore Reddy Venkata Thappeta, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 17/720,855

(22) Filed: Apr. 14, 2022

(65) Prior Publication Data

US 2022/0340689 A1 Oct. 27, 2022

(51) Int. Cl.
C08B 37/08 (2006.01)
A61K 45/06 (2006.01)
A61P 31/04 (2006.01)

(52) U.S. Cl.
CPC ............ C08B 37/003 (2013.01); A61K 45/06 (2013.01); A61P 31/04 (2018.01)

(58) Field of Classification Search
CPC ............................ A61K 31/722; C08B 37/003
See application file for complete search history.

(56) References Cited

U.S. PATENT DOCUMENTS 8,916,542 B2 * 12/2014 Baker ...................... A61P 31/04
435/252.1

OTHER PUBLICATIONS

Yang et al., Biopolymers, 2015, 103(10), p. 539-549. (Year: 2015).*
Yang et al., Carbohydrate Polymers, 2012, 87, p. 202-209. (Year: 2012).*
Younes et al., International Journal of Food Microbiology, 2014, 185, p. 57-63. (Year: 2014).*
Mu et al., Food Control, 2014, 38, p. 215-220. (Year: 2014).*
Tin et al., Int. J. Biol. Sci., 2009, 5(2), p. 153-160. (Year: 2009).*
Hu et al., Bioorganic & Medicinal Chemistry Letters, 2016, 26, p. 4548-4551. (Year: 2016).*
Strathdee et al, "Confronting antimicrobial resistance beyond the COVID-19 pandemic and the 2020 election", pp. 1050-1053 Sep. 29, 2020, https://doi.org/10.1016/S0140-6736(20)32063-8.
Aiello et al, "Antibacterial cleaning and hygiene products as an emerging risk factor for antibiotic resistance in the community", The Lancet, Infectious Diseases, vol. 3, Aug. 2003, http://infection. thelancet.com.
Spellberg et al, "The Future of Antibiotics and Resistance", pp. 299-302, Jan. 24, 2013, DOI: 10.1056/NEJMp1215093.

Tyers et al., "Drug combinations: a strategy to extend the life of antibiotics in the 21st century", pp. 141-155, Mar. 2019, https:// doi.org/10.1038/s41579-018-0141-x.
Bush et al., "Interplay between β-lactamases and new β-lactamases inhibitors", pp. 295-306, May 2019, https://doi.org/10.1038/s41579-019-0159-8.
Pages et al., "The porin and the permeating antibiotic: a selective diffusion barrier in Gram-negative bacteria", pp. 893-903, Dec. 2008, doi: 10.1038/nrmicro1994.
Pages et al., "Inhibitors of efflux pumps in Gram-negative bacteria", pp. 382-39, Aug. 2005, doi:10.1016jmolmed.2005.06.006.
Piddock, "Multidrug-resistance efflux pumps-not just for resistance", pp. 629-636, Aug. 2006, doi:10.1038nrmicro1464.
Hancock, "The bacterial outer membrane as a drug barrier", Trands in Microbiology, vol. 5, No. 1, pp. 37-42, Jan. 1997.
Santos et al., "Advanced Drug Delivery Reviews", ScienceDirect, pp. 136-137 &28-48, Dec. 2017, www.elsevier.com/locate/addr.
Findlay et al., "Cationic Amphipjile, a New Generation of Antimicrobials Inspired by the Natural Antimicrobial Peptide Scaffold", Antimicrobial Agents and Chemotherapy, Oct. 2010, pp. 4049-4058, doi: 10.1128/AAC.00530-10.
Ergene et al., "Biomimetic antimicrobial polymers: recent advances in molecular design", pp. 2407-2427, Mar. 2018, DOI: 10.1039/c8py00012c.
Cai et al., "Effects of Chain Length on Ctotoxicity and Endocytosis of Cationic Polymers", Macromolecules, pp. 2050-2057, pubs.acs. org/Macromolecules.
Chin et al., "A macromolecular approach to eradicate multidrug resistant bacterial infections while mitigation drug resistance onset", Nature Communications, pp. 1-14, DOI: 10.1038/s41467-018-03325-6.
Lam et al., "Combation multidrug-resistan Gram-negative bacteria with structurally nanoengineered antimicrobial peptide polymers", Nature Microbiology, pp. 1-11, DOI: 10.1038/NMICROBIOL.2016. 162.
Zhou et al., "Water-Insensitive Synthesis of Poly-β-Peptides with Defined Architecture", Angewandte, pp. 7240-7244, doi.org/10. 1002/anie.202001697.
Yan et al., "Biodegradable Supramolecular Materials Based on Cationic Polyaspartamides and Pillar[5]arene for Targeting Gram-Positive Bacteria and Mitigating Antimicrobial Resistance", pp. 1-11, DOI: 10.1002/adfm.201904683.
Zhou et al., "Poly(2-Oxazoline)-Based Functional Peptide Mimics: Eradicating MRSA Infections and Persisters while Alleviating Antimicrobial Resistance", Angewandte, DOI: 10.1002/anie. 202000505.

(Continued)

*Primary Examiner* — Jonathan S Lau
(74) *Attorney, Agent, or Firm* — Thomas Horstemeyer, LLP

(57) ABSTRACT

Disclosed herein is a compound of formula I:

where m, n and R$^1$ are as defined herein. Also disclosed herein are uses of the compound.

17 Claims, 7 Drawing Sheets

(56)          References Cited

OTHER PUBLICATIONS

Rabea et al., "Chitosan as Antimicrobial Agent: Application and Mode of Action", DOI:10.1021/bm034130m.

Benhabiles et al., "Antibacterial activity of chitin, chitosan and its oligomer prepared from shrimp shell waste", doi:10.1016/j.foodhyd.2012.02.013.

Ma et al., "Application, mode of action, and in vivo activity of chitosan and its micro- and nanoparticles as antimicrobial agents: A review", http://dx.doi.org/10.1016/j.carbpol.2017.08.082.

Kong et al., "Antimicrobial properties of chitosan and mode of action: A state of the art review", doi: 10.1016/j.ijfoodmicro.2010.09.012.

Vinsova et al., "Chitosan Derivatives with Antimicrobial, Antitumour and Antioxidant Activities—a Review" Current Pharmaceutical Design, 2011, vol. 17, pp. 3596-3607.

Sajomsang et al., "Synthesis of methylated chitosan containing aromatic moieties: Chemoselectivity and effect on molecular weight", doi:10.1016/j.carbpol.2007.10.023.

Zhong et al., "Synthesis of acyl thiourea derivatives of chitosan and their antimicrobial activities in vitro", doi: 10.1016/j.carres.2007.11.024.

Runarsson et al., "tert-Butyldimethylsilyl O-protected chitosan and chitooligosaccharides: useful precursors for N-modification in common organic solvents", doi: 10.1016/j.carres.2008.08.014.

Kurita et al., "N-Phthaloylated Chitosan as an Essential Precursor for Controlled Chemical Modifications of Chitosan: Synthesis and Evaluation", Polymer Journal, vol. 39, No. 9, pp. 945-952, 2007.

Lee et al., "Preparation of chitosan self-aggregates as a gene delivery system", Journal of Controlled Release, 1998, pp. 213-220.

Hou et al., Nanoparticles of Short Cationic Peptidopolysaccharide Self-Assembled by Hydrogen Bondy with Antibacterial Effect against Multidrug-Resistant Bacteria, DOI: 10.1021/acsami.7b12120.

Liu et al., "Chitosan kills bacteria through cell membrane damage", doi: 10.1016/j.ijfoodmicro.2004.01.022.

Mu et al., "Chitosan Improves Anti-Biofilm Efficacy of Gentamicin through Facilitating Antibiotic Penetration", 2014, doi:10.3390/ijms151222296.

Tin et al., "Synergistic Combinations of Chitosans and Antibiotics in Staphylococcus aureus", Letters in Drug Design & Discovery, 2010, vol. 7, 31-35.

Kim et al., "Synergistic Antibacterial Effects of Chitosan-Caffeic Acid Conjugate against Antibiotic-Resistant Acne-Related Bacteria", 2017, doi: 10.3390/md15060167.

Sayed et al., "Expedient synthesis and properties of 6-deoxy-6-amino chitosan", 2018, https://doi.org/10.1016/j.carbpol.2018.05.030.

Je et al., "Chitosan Derivatives Killed Bacterial by Disrupting the Outer and Inner Membrane", 2006, DOI:10.1021/jf061310p.

Assadi et al.,"Novel synergistic activities of tetracycline copper oxide nanoparticles integrated into chitosan micro particles for delivery against multiple drug resistant strains: Generation of reactive oxygen species (ROS) and cell death", https://doi.org/10.1016/j.jddst.2017.11.017.

Satoh et al., "6-Amino-6-deoxy-chitosan. Sequential chemical modifications at the C-6 positions of N-phthaloyl-chitosan and evaluation as a gene carrier", doi: 10.1016/j.carres.2006.06.019.

Richard et al., "Ionization Behavior of Chitosan and Chitosan-DNA Polyplexes Indicate That Chitosan Has a Similar Capability to Induce a Proton-Sponge Effect as PEI", dx.doi.org/10.1021/bm4000713.

Akinc et al., "Explring polyethyleinmine-mediated DNA transfection and the proton sponge hypothesis", 2005, DOI: 10.1002/jgm.696.

Lei et al., "Self-Assembling Myristoylated Human α-Defensin 5 as a Next-Generation Nanobiotics Potentiates Therapeutic Efficacy in Bacterial Infection", 2018, DOI: 10.1021/acsnano.7b09109.

Ren et al., "Effect of intranasal instillation of Escherichia coli on apoptosis of spleen cells in diet-induced-obese mice", 2020, https://doi.org/10.1038/s41598-020-62044-5.

Silva-Santana G et al., "Mice Infection by Methicillin-Resistant Staphylococcus aureus from Different Colonization Sites in Humans Resulting in Difusion to Multiple Organs", 2016, DOI: 10.4172/2161-0681.1000283.

Mwangi et al., "The antimicrobial peptide ZY4 combats multidrugresistant Pseudomonas aeruginosa and Acinetobacter baumannii infection", 2019, www.pnas.org/cgi/doi/10.1073/pnas.1909585117.

Fang et al., "Antibacterial activities of N-alkyl imidazoliumbased poly(ionic liquid) nanoparticles†", 2018, DOI: 10.1039/c8py01290c.

Tan et al., "Synthesis, characterization, and antibacterial property of navel starch derovatives wotj 1, 2, 3,-trizole", 2016, http://dx.doi.org/10.1016/j.carbpol.2016.01.007.

Schillen et al., "Micellar Sphere-to-Rod Transition in an Aqueous Triblock Copolymer System. A Dynamic Light Scattering Study of Translational and Rotational Diffusion", Department of Physical Chemistry, Macromolecules, vol. 27, pp. 4825-4832, 1994.

Thappeta et al., "Combined Efficacy of an Antimicrobial Cationic Peptide Polymer with Conventional Antibiotics to Combat Multidrug-Resistant Pathogens", 2020, https://dx.doi.org/10.1021/acsinfecdis.0c00016.

Si et al., "AGlycosylated Cationic Block Poly(β-peptide) Reverses Intrinsic Antibiotic Resistance in All ESKAPE Gram-Negative Bacteria", 2020, DOI: 10.1002/anie.201914304.

Durand-Reville et al., "ETX2514 is a broad-spectrum β-lactamase inhibitor for the treatment of drug-resistant Gram-negative bacteria including Acinetobacter baumannii", 2017, DOI: 10.1038/nmicrobiol.2017.104.

Yang et al., "Preparation, characterization and antimicrobial activity of 6-amino-6-deoxychitosan", 2012, doi:10.1016/j.carbpol.2011.07.039.

Si et al., "Antimicrobial Effect of a Novel Chitosan Derivative and Its Synergistic Effect with Antibiotics", 2021, https://dx.doi.org/10.1021/acsami.0c20881.

Stokes et al., "Pentamidine sensitizes Gram-negative pathogens to antibiotics and overcomes acquired colistin resistance" 2017, DOI: 10.1038/nmicrobiol.2017.28.

Lewis, "The Science of Antibiotic Discovery", 2020, https://doi.org/10.1016/j.cell.2020.02.056.

Jean-Paul Behr, "The Proton Sponge: a Trick to Enter Cells the Virus Did Not Exploit", ILMAC 96: 1st Swiss Cost Chemistry Symposium, CHIMA 51 (1997).

M. M. AbdElhady, Preparation and Characterization of Chitsan/Zinc Oxide Nanoparticles for Imparting Antimicrobial and UV Protection to Cotton Fabric, doi: 10.1155/2012/840591.

Badawy et al., "A Biopolymer Chitosan and Its Derivatives as Promising Antimicrobial Agents against Plant Pathogens and Their Application in Crop Protection", doi: 10.1155/2011/460381.

Younes et al., "Chitin and Chitosan Preparation from Marine Sources. Structure, Properties, and Applications", doi: 10.3390/md13031133.

Huang et al., "Alpha-helical cationic antimicrobial peptides: relationships of structure and function", Key Laboratory for Molecular Enzymology and Engineering of Ministry of Education, Jilin University, DOI: 10.1007/s13238-010-0004-3. Protein Cell, 2010, 1(2), p. 143-152.

* cited by examiner (A)                    AB-1

(B)                MRSA USA300

(C)                    PAO1

CHITOSAN DERIVATIVES AS ANTIMICROBIALS AND SYNERGISTIC COMBINATIONS THEREOF

CROSS-REFERENCE TO RELATED APPLICATIONS

This application claims priority to, and the benefit of, Singapore Patent Application SG10202103862T, filed on Apr. 15, 2021, which is incorporated by reference as if set forth herein in its entirety.

FIELD OF INVENTION

The current invention relates to derivatives of chitosan, which display an antimicrobial effect—not only when applied as the only active ingredient, but also provides a synergistic antimicrobial effect when used in combination with another antimicrobial compound.

BACKGROUND

The listing or discussion of a prior-published document in this specification should not necessarily be taken as an acknowledgement that the document is part of the state of the art or is common general knowledge.

Nowadays, the development of bacteria resistance towards antibiotics is emerging as a severe healthcare problem. After decades of antibiotic abuse as drugs or detergents, bacteria have developed antibiotic resistance mechanisms, such as alternating the target protein of the antibiotics, secreting enzymes to degrade the antibiotics, changing membrane permeability to prevent antibiotics influx, and developing membrane efflux pumps to exclude the antibiotics inside bacteria. The bacterial cell membranes function as barriers for antibiotics. Inspired by natural antimicrobial peptides, membrane-targeting cationic antimicrobial polymers provide a novel approach in curing bacterial infection (B. Findlay, G. G. Zhanel & F. Schweizer, *Antimicrob. Agents Chemother.* 2010, 54, 4049-4058). Combined with the hydrophobic moiety, the cationic polymer can interrupt cytoplasmic membrane and cause the leakage of cytosol, resulting in the death of bacteria (C. Ergene, K. Yasuhara & E. F. Palermo, *Polym. Chem.* 2018, 9, 2407-2427). However, the reported cationic antimicrobial polymers have low biocompatibility in general as measured by high hemolytic activity and cytotoxicity towards mammalian cells (J. Cai et al., *Macromolecules* 2011, 44, 2050-2057). Although the progress in this area has discovered some biocompatible cationic antimicrobial polymers based on polycarbonate (W. Chin et al., *Nat. Commun.* 2018, 9, 1-14), α-peptide (S. J. Lam et al., *Nat. Microbiol.* 2016, 1, 1-11), β-peptide (M. Zhou et al., *Angew. Chem. Int. Ed.* 2020, 59, 7240-7244), polyaspartamide (S. Yan et al., *Adv. Funct. Mater.* 2019, 29, 1904683), poly(2-oxazoline) (M. Zhou et al., *Angew. Chem. Int. Ed.* 2020, 59, 6412-6419), etc., most of them share the general design principle of balanced cationic and hydrophobic residues. Therefore, it is critical to search and develop cationic antimicrobial polymers with good biocompatibility based on new design.

Chitosan is a cationic polysaccharide derived from chitin, the main component in many natural materials. Chitosan has certain amount of antimicrobial activity via membrane interruption (E. I. Rabea et al., *Biomacromolecules* 2003, 4, 1457-1465; and M. S. Benhabiles et al., *Food Hydrocoll.* 2012, 29, 48-56) and has been applied as a defensive material to different animals in agriculture (Z. Ma, A.

Garrido-Maestu & K. C. Jeong, *Carbohydr. Polym.* 2017, 176, 257-265). Various forms of chitosan and its derivatives such as pure chitosan (M. Kong et al., *Int. J. Food Microbiol.* 2010, 144, 51-63), quaternary ammonium chitosan (J. Vinš-ová & E. Vavříková, *Curr. Pharm. Des.* 2011, 17, 3596-3607), chitosan grafted with quaternary pyridinium (W. Sajomsang et al., *Carbohydr. Polym.* 2008, 72, 740-750), phosphonium and sulphonamide groups (Z. Zhong et al., *Carbohydr. Res.* 2008, 343, 566-570) have been reported for antimicrobial applications (Ö. V. Rúnarsson et al., *Carbohydr. Res.* 2008, 343, 2576-2582; and K. Kurita et al., *Polym. J.* 2007, 39, 945-952). However, the toxicities of such chitosan derivatives are still high due to the introduction of hydrophobic moieties together with cationic charges; the hydrophobic side groups also limit the application of the chitosan derivatives as antimicrobial agents in water due to reduced solubility. On the other hand, chitosan backbones tend to aggregate by formation of hydrogen bonds (K. Y. Lee et al., *J. Control. Release* 1998, 51, 213-220), and the aggregated chitosan nanoparticle without hydrophobic moieties functions as a cationic proton sponge, which can be used as an effective antimicrobial agent with high biocompatibility (Z. Hou et al., *ACS Appl. Mater. Interfaces* 2017, 9, 38288-38303). However, even though the antimicrobial effects of chitosan and its derivatives are well-reported, the efficacies are generally weak, making the bottleneck of real application of chitosan and its derivatives as antimicrobial agents (Z. Ma, A. Garrido-Maestu & K. C. Jeong, *Carbohydr. Polym.* 2017, 176, 257-265).

Due to their unique membrane interruption ability (H. Liu et al., *Int. J. Food Microbiol.* 2004, 92, 147-155), cationic polysaccharides based on chitosan and its derivatives are good candidates to effectively sensitize the multi-drug resistant (MDR) bacteria to classical antibiotics. Chitosan is reported to sensitize a broad-spectrum of Gram-positive and Gram-negative bacteria to a wide range of antibiotic agents such as gentamicin (H. Mu et al., Int. *J. Mol. Sci.* 2014, 15, 22296-22308), ceftriaxone, sulfamethoxazole, tetracycline (S. Tin et al., *Lett. Drug Des. Discov.* 2010, 7, 31-35) and caffeic acid (J. -H. Kim et al., *Mar. Drugs* 2017, 15, 167), but the synergistic potency is limited by the low solubility of chitosan (S. Tin et al., *Lett. Drug Des. Discov.* 2010, 7, 31-35). On the other hand, modifications of chitosan can further improve its solubility (S. Sayed, T. Millard & A. Jardine, *Carbohydr. Polym.* 2018, 196, 187-198) and membrane interruption potency (J. -Y. Je & S. -K. Kim, *J. Agric. Food Chem.* 2006, 54, 6629-6633). Further, chitosan backbones tend to aggregate which provides more versatility to fabricate nanoparticle formulation of chitosan for synergizing with antibiotics (Z. Assadia, G. Emtiazib & A. Zarrabia, *J. Drug Deliv. Sci. Technol.* 2018, 44, 65-70). Nonetheless, even though the synergy between pure chitosan and antibiotics are recently published, the synergy between modified chitosan derivatives and antibiotics are still not reported.

Therefore, there exists a need to discover new antibacterial chitosan derivatives that demonstrate synergistic effect with antibiotics.

SUMMARY OF INVENTION

Aspects and embodiments of the current invention will now be discussed by reference to the following numbered clauses.

3

1. A compound of formula I:

where

I the sum of m and n is 1 and each of m and n is from 0.1 to 0.9;

each $R_1$ is selected from $NH_2$, $NH$—$(CH_2)_a$—X, where each wiggly line represents the point of attachment to the rest of the compound;

a is 2 to 3;

X is selected from O—$(CH_2)_2$—O—$(CH_2)_2$—$NH_2$, $NH_2$, $NH$—$(CH_2)_b$—Y, $N((CH_2)_c$—$NH_2)_2$, and where the wiggly line represents the point of attachment to the rest of the compound;

b and c are each independently selected from 2 to 4,

Y is selected from $NH_2$ or $NH$—$(CH_2)_d$—$NH_2$, d is selected from 2 to 4, or a pharmaceutically acceptable salt or solvate thereof.

2. The compound according to Clause 1, wherein m is 0.8 and n is 0.2.

3. The compound according to Clause 1 or Clause 2, wherein the compound of formula I, or a pharmaceutically acceptable salt or solvate thereof, is selected from the list:

4

-continued

-continued

4. The compound according to any one of Clauses 1 to 3, wherein the compound of formula I or a pharmaceutically acceptable salt or solvate thereof is:

5. A pharmaceutical composition comprising a compound of formula I or a pharmaceutically acceptable salt or solvate thereof according to any one of Clauses 1 to 4, and a pharmaceutically acceptable carrier.

6. The pharmaceutical composition according to Clause 5, wherein the composition further comprises one or more pharmaceutically acceptable excipients and adjuvants.

7. A compound of formula I or a pharmaceutically acceptable salt or solvate thereof according to any one of Clauses 1 to 4 for use in medicine.

8. A method of treating or preventing a microbial infection in a subject, the method comprising administering a pharmaceutically effective amount of a compound of formula I or a pharmaceutically acceptable salt or solvate thereof according to any one of Clauses 1 to 4.

9. A compound of formula I or a pharmaceutically acceptable salt or solvate thereof according to any one of Clauses 1 to 4 for use in treating or preventing a microbial infection.

10. Use of a compound of formula I or a pharmaceutically acceptable salt or solvate thereof according to any one of Clauses 1 to 4 in the preparation of a medicament for treating or preventing a microbial infection.

11. A method of treating or preventing a microbial infection in a subject, the method comprising administering a pharmaceutically effective amount of a compound of formula I or a pharmaceutically acceptable salt or solvate thereof according to any one of Clauses 1 to 4, and an antibiotic or a pharmaceutically acceptable salt or solvate thereof, wherein the compound of formula I is administered sequentially, simultaneously or concomitantly with the antibiotic.

12. A compound of formula I or a pharmaceutically acceptable salt or solvate thereof according to any one of Clauses 1 to 4 and an antibiotic or a pharmaceutically acceptable salt or solvate thereof, for use in treating or preventing a microbial infection, wherein the compound of formula I is administered sequentially, simultaneously or concomitantly with the antibiotic to a subject.

13. Use of a compound of formula I or a pharmaceutically acceptable salt or solvate thereof according to any one of Clauses 1 to 4 and an antibiotic or a pharmaceutically acceptable salt or solvate thereof, in the preparation of a medicament for treating or preventing a microbial infection.

14. The method according to Clause 11, the compound for use according to Clause 12 and the use according to Clause 13, wherein the antibiotic is selected from one or more of the group consisting of ampicillin, carbenicillin, meropenem, novobiocin, tobramycin, amikacin, tazobactam, and rifampicin, or a pharmaceutically acceptable salt or solvate thereof.

15. A pharmaceutical composition comprising a compound of formula I or a pharmaceutically acceptable salt or solvate thereof according to any one of Clauses 1 to 4 and an antibiotic or a pharmaceutically acceptable salt or solvate thereof, and a pharmaceutically acceptable carrier.

16. The pharmaceutical composition according to Clause 15, wherein the composition further comprises one or more pharmaceutically acceptable excipients and adjuvants.

17. A kit of parts comprising:
(a) a pharmaceutical composition comprising a compound of formula I or a pharmaceutically acceptable salt or solvate thereof according to any one of Clauses 1 to 4, and a pharmaceutically acceptable carrier; and
(b) a pharmaceutical composition comprising an antibiotic or a pharmaceutically acceptable salt or solvate thereof, and a pharmaceutically acceptable carrier.

18. The kit of parts according to Clause 17, wherein each of the pharmaceutical compositions further comprises one or more pharmaceutically acceptable excipients and adjuvants.

19. The kit of parts according to Clause 17 or Clause 18, wherein the antibiotic is selected from one or more of the group consisting of ampicillin, carbenicillin, meropenem, novobiocin, tobramycin, amikacin, tazobactam, and rifampicin, or a pharmaceutically acceptable salt or solvate thereof.

DRAWINGS

Gram-positive bacteria MRSA USA300; and (C) Gram-negative bacteria *P. aeruginosa* PAO1 at 1×MIC, 2×MIC and 4×MIC.

Figure 4:
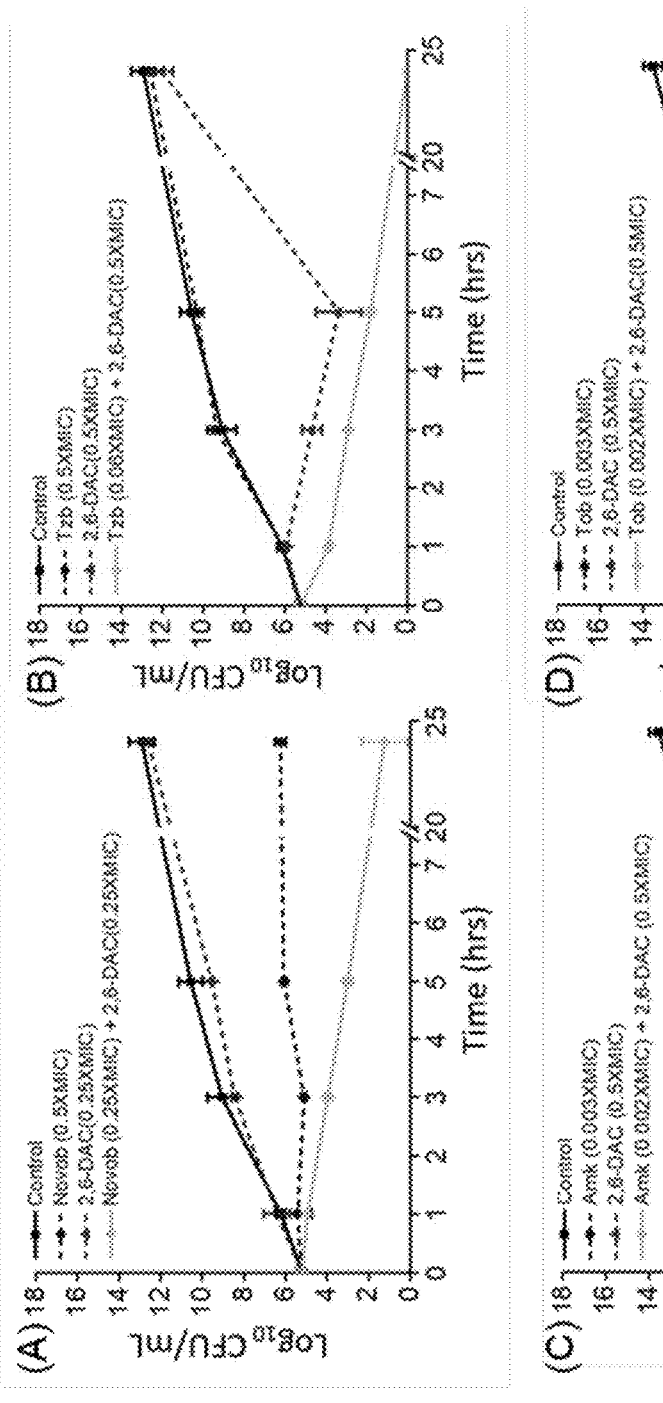
Figure 4:
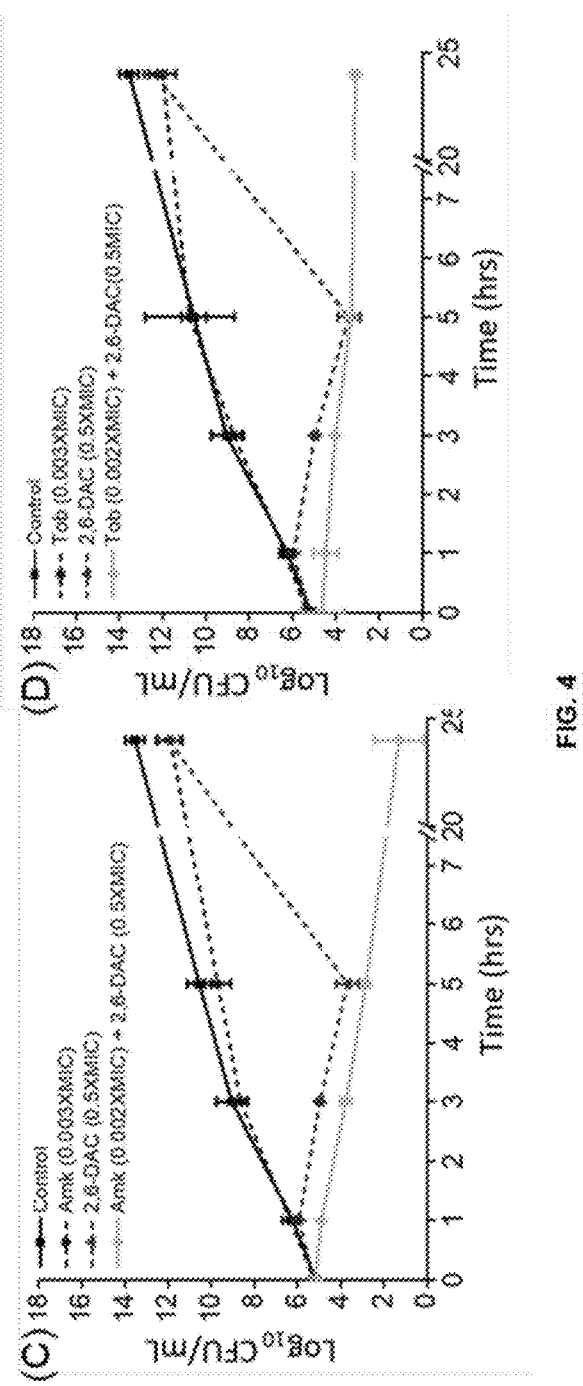

FIG. 4 depicts the time-killing assay of 2,6-DAC in synergistic combination with various antibiotics against *A. baumannii* AB-1. (A) Novobiocin (Novob); (B) Tazobactam (Tzb); (C)

Amikacin (Amk); and (D) Tobramycin (Tob).

Figure 5:
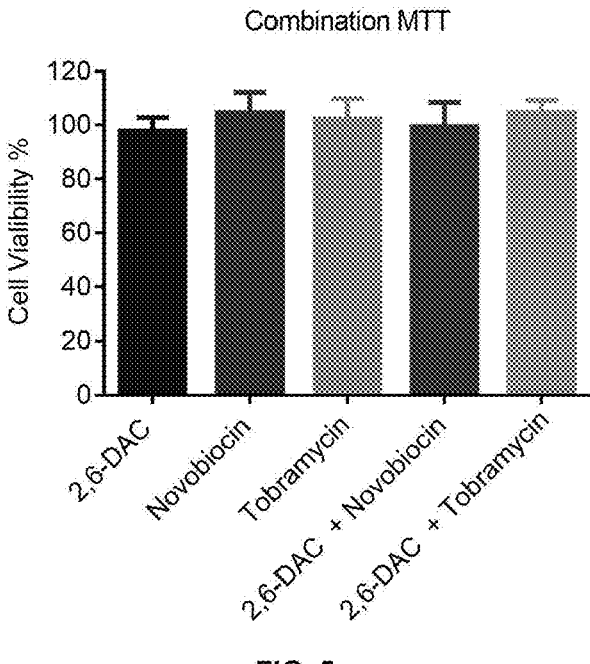

FIG. 5 depicts the in vitro cytotoxicity of 2,6-DAC alone (8 μg/mL), novobiocin alone (0.5 μg/m L), tobramycin alone (2 μg/mL) and their combination of 2,6-DAC (8 μg/m L)+novobiocin (0.5 μg/mL) and 2,6-DAC (8 μg/mL)+tobramycin (2 μg/mL) against mammalian NIH 3T3 cells.

Figure 6:
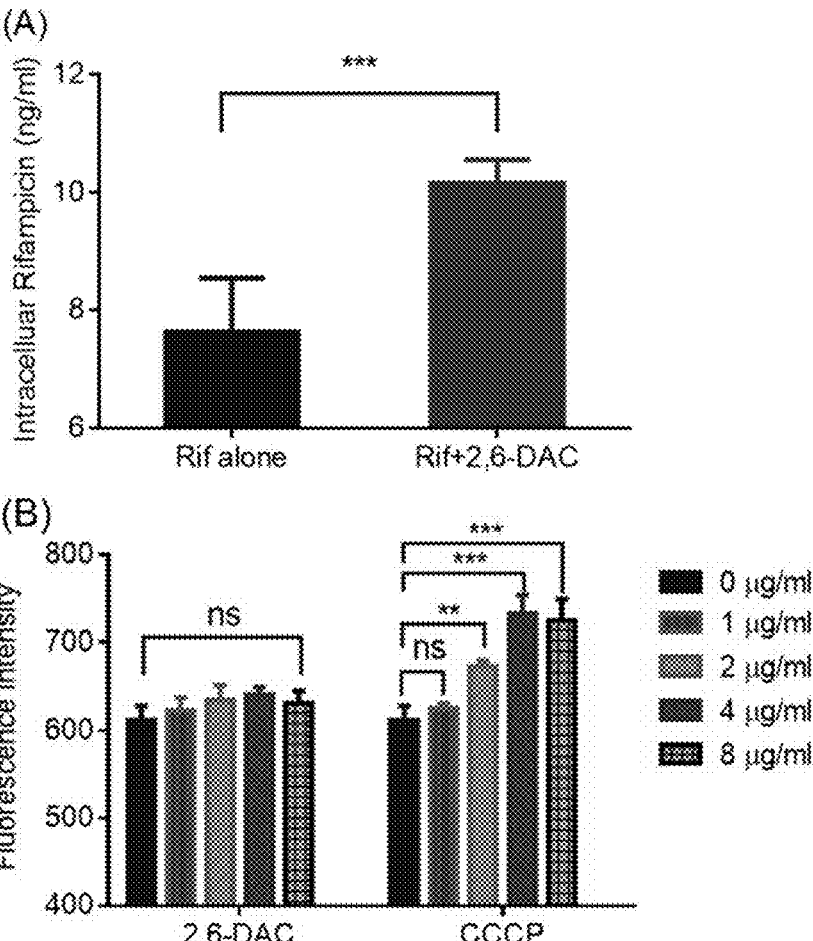

FIG. 6 depicts the mechanism of synergistic combination of 2,6-DAC with antibiotics. (A) Drug accumulation inside *A. baumannii* AB-1 treated by rifampicin alone (2 μg/mL) or with a combination of rifampicin (2 μg/mL)+2,6-DAC (8 μg/mL) that was quantified by liquid chromatography mass spectrometry (LC-MS). Data are expressed as mean±standard deviation; and (B) 2,6-DAC did not inhibit the ethidium bromide efflux in *A. baumannii* AB-1, carbonyl cyanide m-chlorophenyl hydrazone (CCCP) used as positive control. The fluorescence intensity was recorded by TECAN fluorescence spectrometer; ethidium bromide was 16 μg/ml. Data are expressed as mean±standard deviation.

Figure 7:
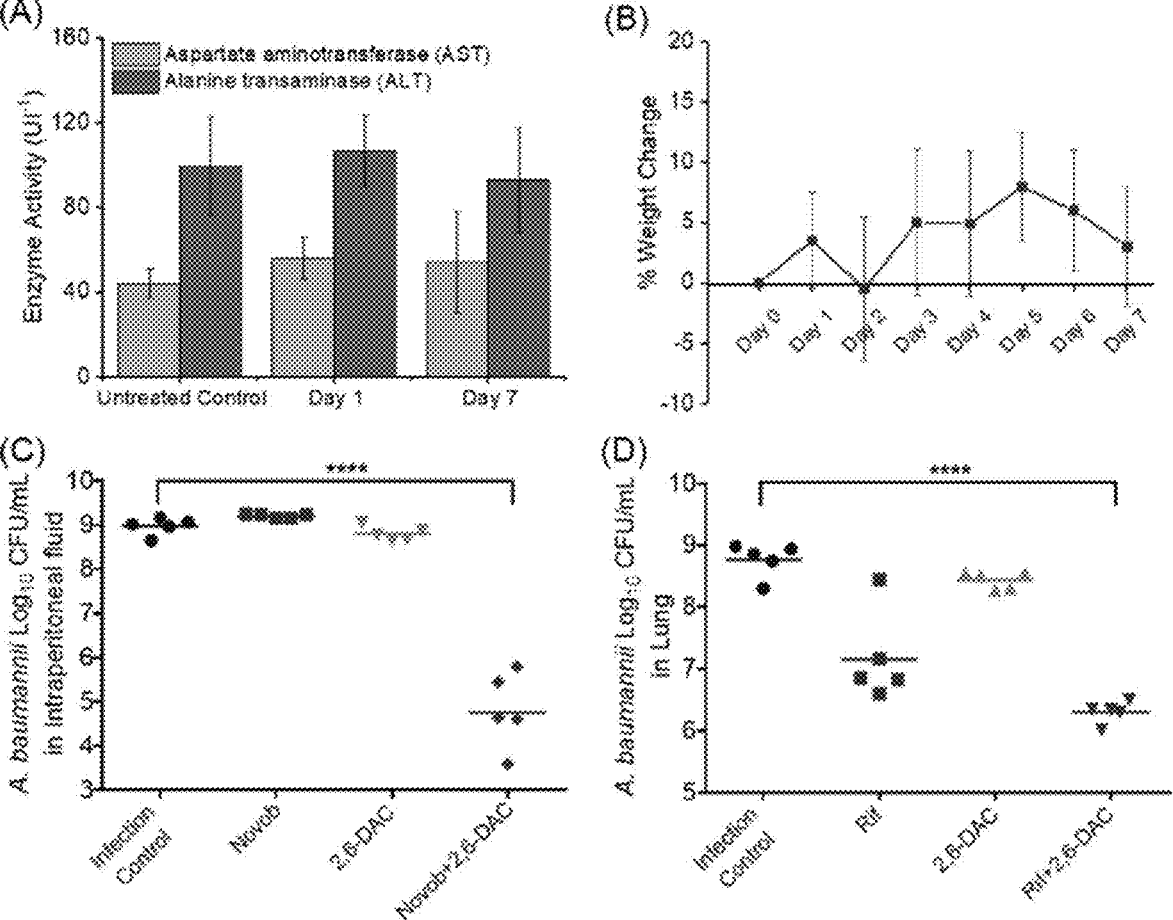

FIG. 7 depicts (A) biomarkers related to kidney and liver functions before (untreated control), 1 day and 7 days after intraperitoneal injection at 25 mg/kg; (B) weight change of mice after oral administration of 100 mg/kg 2,6-DAC; (C) in vivo efficacy of combination of 2,6-DAC with Novob in intraperitoneal infection model. The infection was treated by either PBS control, 10 mg/kg Novob, 25 mg/kg 2,6-DAC alone or their combination (2,6-DAC+Novob); and (D) in vivo efficacy of combination of 2,6-DAC with rifampicin (Rif) in lung infection model. The infection was treated by either PBS control, 10 mg/kg Rif, 25 mg/kg 2,6-DAC alone or their combination (2,6-DAC+Rif). Statistical analysis used one-way ANOVA via GraphPad Prism 6.0.

Figure 8:
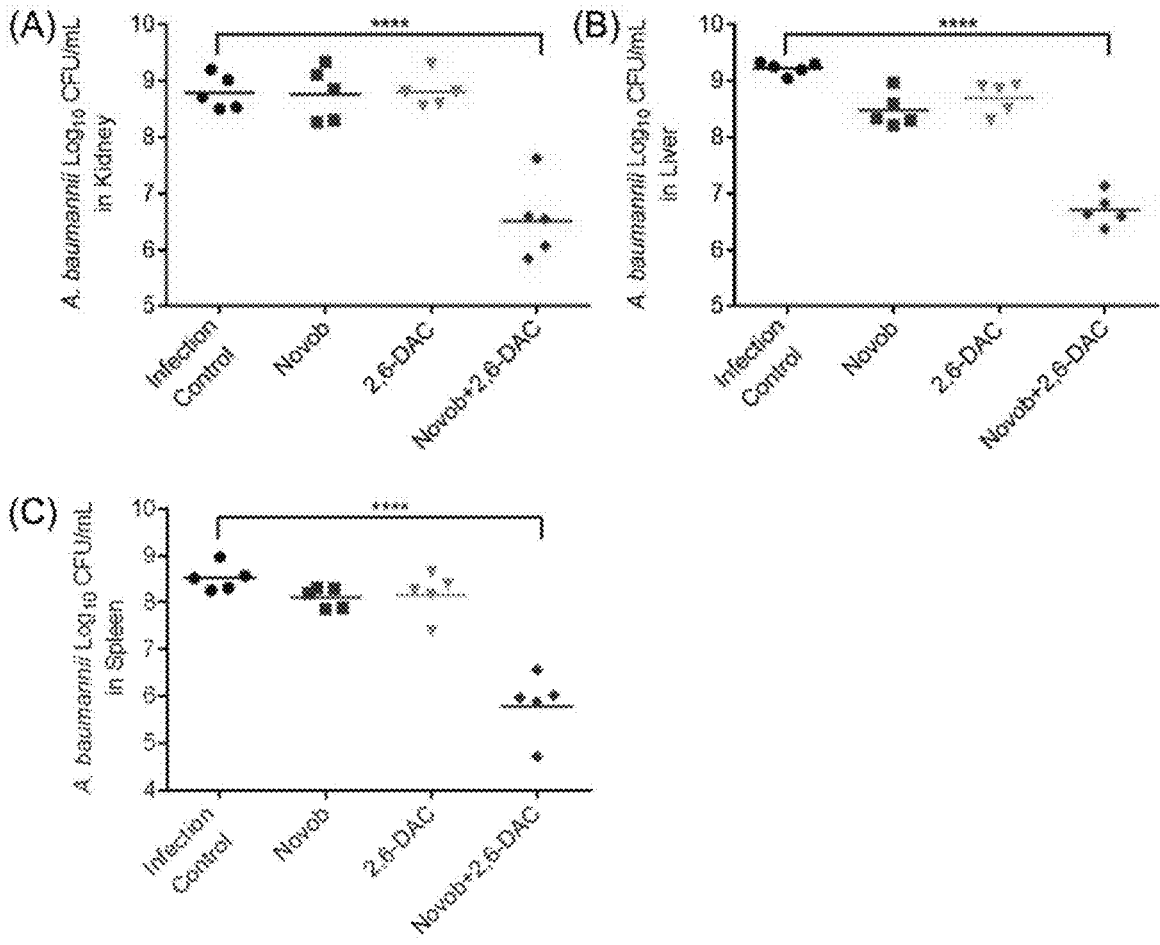

FIG. 8 depicts the in vivo efficacy of 2,6-DAC tested in intraperitoneal infection model. (A) Kidney infection; (B) Liver infection; and (C) Spleen infection. Statistical analysis used one-way ANOVA via GraphPad Prism 6.0.

Figure 9:
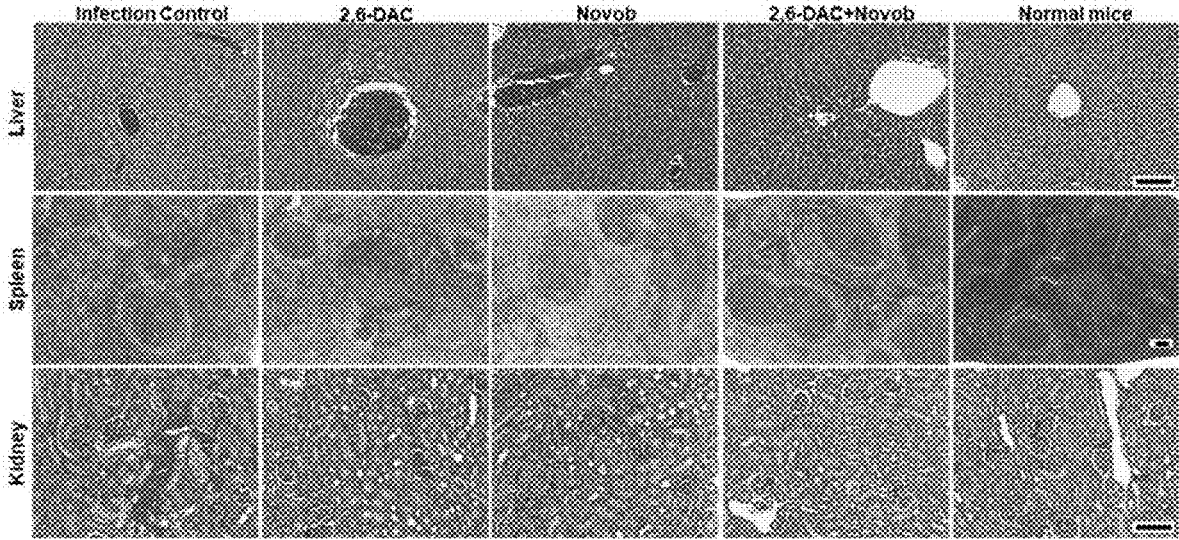

FIG. 9 depicts the histopathological hematoxylin & eosin (H&E) staining of liver, spleen and kidneys from infection control, 2,6-DAC alone, Novob alone and their combination (2,6-DAC+Novob) in intraperitoneal infection model; normal mice used as comparison. Scale bar=100 μm.

Figure 10:
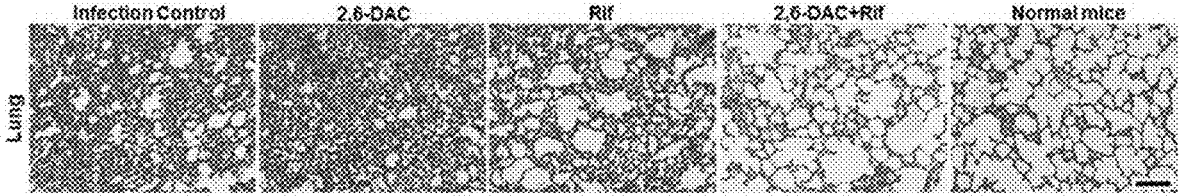

FIG. 10 depicts the histopathological H&E staining of lung from infection control, 2,6-DAC alone, Rif alone and their combination (2,6-DAC+Rif) in lung infection model; normal mice used as comparison. Scale bar=100 μm.

DESCRIPTION

It has been surprisingly found that certain chitosan derivatives have broad antimicrobial activity. In addition, it has been surprisingly found that these chitosan derivatives have a synergistic effect when combined with other antimicrobial agents. Thus, in a first aspect of the invention, there is provided a compound of formula I:

where:
the sum of m and n is 1 and each of m and n is from 0.1 to 0.9;
each $R_1$ is selected from $NH_2$, NH—$(CH_2)_a$—X, where each wiggly line represents the point of attachment to the rest of the compound;
a is 2 to 3;
X is selected from O—$(CH_2)_2$—O—$(CH_2)_2$—$NH_2$, $NH_2$, NH—$(CH_2)_b$—Y, N($(CH_2)_c$—$NH_2)_2$, and where the wiggly line represents the point of attachment to the rest of the compound;
b and c are each independently selected from 2 to 4,
Y is selected from $NH_2$ or NH—$(CH_2)_d$—$NH_2$,
d is selected from 2 to 4,
or a pharmaceutically acceptable salt or solvate thereof.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The phrase, "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure.

As used herein, the singular forms "a," "an," and "the" include plural referents unless the context clearly dictates otherwise.

References herein (in any aspect or embodiment of the invention) to compounds of formula I include references to such compounds per se, to tautomers of such compounds, as well as to pharmaceutically acceptable salts or solvates, or pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (–)-L-malic), malonic, (±)-DL-mandelic, meta-phosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g.(+)-L-tartaric), thiocyanic, undecylenic and valeric acids.

Particular examples of salts are salts derived from mineral acids such as hydrochloric, hydrobromic, phosphoric, meta-phosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by compounds of formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs,* Second Edition, published by SSCI, Inc of West Lafayette, IN, USA, 1999, ISBN 0-967-06710-3.

"Pharmaceutically functional derivatives" of compounds of formula I as defined herein includes ester derivatives and/or derivatives that have, or provide for, the same biological function and/or activity as any relevant compound of the invention. Thus, for the purposes of this invention, the term also includes prodrugs of compounds of formula I.

The term "prodrug" of a relevant compound of formula I includes any derivative that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. I-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Further embodiments of the invention that may be mentioned include those in which the compound of formula I is isotopically labelled. However, other, particular embodiments of the invention that may be mentioned include those in which the compound of formula I is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I. Thus, the term "isotopically labelled" includes references to compounds of formula I that are isotopically enriched at one or more positions in the compound.

The isotopic labelling or enrichment of the compound of formula I may be with a radioactive or non-radioactive isotope of any of hydrogen, carbon, nitrogen, oxygen, sulfur, fluorine, chlorine, bromine and/or iodine. Particular isotopes that may be mentioned in this respect include $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{37}$Cl, $^{77}$Br, $^{82}$Br and $^{125}$I).

When the compound of formula I is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

As will be appreciated, the compounds of formula I include two repeating units. It will be appreciated that these repeating units may be presented in any suitable combination within the compounds of formula I disclosed herein. Thus, they may be presented as random copolymers, block copolymers and the like. The values of m and n refer to the relative proportions of these subunits present in the compounds of formula I and are intended to add up to 1. Thus, in the first aspect of the invention, m can have a value of from 0.1 to 0.9, with n having a corresponding value that adds up to 1, or vice versa. In particular embodiments that may be mentioned herein, m may be 0.8 and n may be 0.2.

For the avoidance of doubt, in compounds of the invention where there is more than one of a substituent or a chosen length for a carbon chain, then each of those instances may be independently selected from one another. For example, for compounds of formula I where $R_1$ is $NH$—$(CH_2)_a$—$X$ and X is $N$—$((CH_2)_c$—$NH_2)_2$, then the value for each c may be independently selected from 2 to 4. For example, one c may be 2 and the other c may be 4.

The compounds of formula I may have any suitable molecular weight. For example, the compounds of formula I may have a number average molecular weight of from 5,000 to 20,000 Daltons, such as from 7,000 to 15,000 Daltons, such as about 12,850 Daltons. The polydispersity of the compounds of formula I may be from 1.0 to 2.0, such as about 1.50, as measured using gel permeation chromatography.

In embodiments of the invention that may be mentioned herein, the compound of formula I, or a pharmaceutically acceptable salt or solvate thereof, may be selected from the list:

-continued

In more particular embodiments of the invention, the compound of formula I or a pharmaceutically acceptable salt or solvate thereof may be:

As will be appreciated, the compounds of formula I or a pharmaceutically acceptable salt or solvate thereof may be used in the treatment of microbial infections. Thus, in a further aspect of the invention, there is provided a pharmaceutical composition comprising a compound of formula I or a pharmaceutically acceptable salt or solvate thereof as described hereinbefore, and a pharmaceutically acceptable carrier. In certain embodiments that may be mentioned herein, this composition may further comprise one or more pharmaceutically acceptable excipients and adjuvants.

Compounds of formula I may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy,* 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula I in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

The compound of formula I mentioned above may be utilised in a method of medical treatment.

Thus, according to a further aspect of the invention, there is provided a compound of formula I or a pharmaceutically acceptable salt or solvate thereof as described hereinbefore for use in medicine. In further aspects, there is provided:

(AI) a method of treating or preventing a microbial infection in a subject, the method comprising administering a pharmaceutically effective amount of a compound of formula I or a pharmaceutically acceptable salt or solvate thereof as described hereinbefore;

(AII) a compound of formula I or a pharmaceutically acceptable salt or solvate thereof as described hereinbefore for use in treating or preventing a microbial infection;

(AIII) a compound of formula I or a pharmaceutically acceptable salt or solvate thereof as described hereinbefore in the preparation of a medicament for treating or preventing a microbial infection.

As mentioned above, the compounds of formula I may be used in combination with other antibiotic agent to provide a synergistic treatment effect. Thus, in further aspects of the invention, there is provided:

(BI) a method of treating or preventing a microbial infection in a subject, the method comprising administering a pharmaceutically effective amount of a compound of formula I or a pharmaceutically acceptable salt or solvate thereof as described hereinbefore, and an antibiotic or a pharmaceutically acceptable salt or solvate thereof, wherein the compound of formula I is administered sequentially, simultaneously or concomitantly with the antibiotic;

(BII) a compound of formula I or a pharmaceutically acceptable salt or solvate thereof as described hereinbefore and an antibiotic or a pharmaceutically acceptable salt or solvate thereof, for use in treating or preventing a microbial infection, wherein the compound of formula I is administered sequentially, simultaneously or concomitantly with the antibiotic to a subject;

(BIII) use of a compound of formula I or a pharmaceutically acceptable salt or solvate thereof as described hereinbefore and an antibiotic or a pharmaceutically acceptable salt or solvate thereof, in the preparation of a medicament for treating or preventing a microbial infection.

In the combinations mentioned above, the antibiotic agent may be any suitable agent. For example, the antibiotic may be selected from one or more of the group consisting of ampicillin, carbenicillin, meropenem, novobiocin, tobramycin, amikacin, tazobactam, and rifampicin, or a pharmaceutically acceptable salt or solvate thereof.

In additional embodiments of the invention, there is provided a pharmaceutical composition comprising a compound of formula I or a pharmaceutically acceptable salt or solvate thereof as described hereinbefore and an antibiotic or a pharmaceutically acceptable salt or solvate thereof, and a pharmaceutically acceptable carrier. This pharmaceutical composition may further comprise one or more pharmaceutically acceptable excipients and adjuvants. As will be appreciated, details of how to manufacture such pharmaceutical formulations are provided above.

In a further aspect of the invention, there is provided a kit of parts comprising:

(a) a pharmaceutical composition comprising a compound of formula I or a pharmaceutically acceptable salt or solvate thereof as described hereinbefore, and a pharmaceutically acceptable carrier; and (b) a pharmaceutical composition comprising an antibiotic or a pharmaceutically acceptable salt or solvate thereof, and a pharmaceutically acceptable carrier.

As will be appreciated, each pharmaceutical composition of the kit of parts may further comprise one or more pharmaceutically acceptable excipients and adjuvants, where each composition may be obtained as described hereinbefore.

The antibiotic in the kit of parts may be any suitable antibiotic. For example, the antibiotic may be selected from one or more of the group consisting of ampicillin, carbenicillin, meropenem, novobiocin, tobramycin, amikacin, tazobactam, and rifampicin, or a pharmaceutically acceptable salt or solvate thereof.

Further aspects and embodiments of the current invention will now be discussed by reference to the following non-limiting examples.

EXAMPLES

Materials

Low molecular weight chitosan (200 KDa), phthalic anhydride, N-methyl pyrrolidinone, N-bromosuccinimide (NBS), triphenylphosphine (TPP), sodium azide ($NaN_3$), hydrazine monohydrate, anhydrous N,N-dimethylformamide, sodium hydroxide (NaOH), 3,5-amino-1,2,4-triazole, 3-amino-1,2,4-triazole, 5-aminoimidazole-4-carbonitrile, spermine, ethylene diamine, diethylenetriamine, tris(2-aminoethyl)amine, ethylene glycol (EG)-bis-(2-aminoethyl) ether, 1-(3-aminopropyl)imidazole, ethanol (EtOH), acetone, hydrochloric acid (HCl), ofloxacin, levofloxacin, azithromycin, erythromycin, meropenem, imipenem, ertapenem, doripenem, cephalothins, cefoxitin, ceftazidime, ceftriaxone, ramoplanin, amoxicillin, ampicillin, carbenicillin, novobiocin, tobramycin, trimethoprim, ceftazidime, chloramphenicol, ciprofloxacin, piperacillin, polymyxin B, amikacin, colistin, gramicidin, tazobactam, ethidium bromide, methanol, neutral buffered formalin, carbonyl cyanide m-chlorophenyl hydrazine (CCCP), formic acid, sodium acetate (NaOAc), acetic acid (AcOH), acetonitrile, were purchased from Sigma-Aldrich Corp and used without further purification. Paraffin and hematoxylin & eosin (H&E) were given by Institute of Molecular and Cell Biology. A*STAR, Singapore. Luria-Bertani (LB) agar and Mueller-Hinton broth (MHB) were purchased from BD Difco™. Phosphate-buffered saline (PBS) was purchased from Invitrogen. 3T3 cells were purchased from ATCC (#CRL-1658™).

Bacteria: *Pseudomonas aeruginosa* PAO1, S. aureus ATCC 29213, MRSA USA300, *L. monocytogenes, P. aeruginosa* BAA2797, and *K. pneumoniae* BAA2784, *Acinetobacter baumannii* (ATCC17978 and BAA-2803) were from ATCC. *Acinetobacter baumannii* AB-1 was obtained from from Tan Tock Seng Hospital, Singapore.

Analytical Techniques

Nuclear Magnetic Resonance (NMR) Spectroscopy

$^1$H NMR spectra are recorded at 25° C. on a Bruker AV300 NMR spectrometer at 300 MHz. Chemical shifts ($\delta$) are reported in parts per million (ppm) with reference to the internal standard protons of tetramethyl silane (TMS).

Gel Permeation Chromatography (GPC)

The molecular weight and molecular weight distribution were measured using a Waters' GPC system equipped with a 2410 refractive index detector (RID), using two ultrahydrogel columns and sodium acetate buffer (0.5 M of NaOAc and 0.5 M of AcOH, pH ~4.5) as mobile phase at 40° C. with a flow rate of 0.5 mL/min. Narrow dispersed pullulan standards were used as reference.

LC-MS

LC-MS data was obtained on an Agilent 6130 LC-MS machine with BEH C18 column, using water and acetonitrile with 0.1% formic acid as mobile phase at 40° C. with a flow rate of 0.3 mL/min.

Example 1

Synthesis of 2,6-Diamino Chitosan (2,6-DAC, Compound 5a)

The synthesis of Compound 5a is shown below (T. Satoh et al., *Carbohydr. Res.* 2006, 341, 2406-2413). Briefly, the intermediate 6-bromo-N-phthaloyl chitosan (Compound 3) was synthesized by phthalic protection of the amino group on chitosan followed by substitution of the hydroxyl group on the 6-position of chitosan to bromide group by N-bromosuccinimide. The bromide group in Compound 3 was converted to the azido group ($N_3$) and further reduced to amino group.

Synthesis of N-phthaloyl chitosan (Compound 2) and Compound 3

1

2

3

Compound 2

N-Phthaloyl chitosan preparation follows the procedure reported (Z. Hou et al., *ACS Appl. Mater. Interfaces* 2017, 9, 38288-38303). To chitosan 1 (5 g, 27.93 mmol), anhydrous DMF (100 mL) was added and the mixture was bath-sonicated (bath preheated at 80° C.) for 1 h under Ar atmosphere. Then, the mixture was stirred at 80° C. for 1 h to fully dissolve the chitosan. The solution was reacted with phthalic anhydride (13.8 g, 93.2 mmol) at 130° C. for 24 h under Ar atmosphere, then cooled to room temperature (rt), precipitated in DI water (500 mL), and filtered. The product was washed repeatedly with water, ethanol and acetone, and vacuum dried overnight at 60° C. to give Compound 2. The NMR analysis shows that >96% of chitosan amine groups are phthaloyl-protected.

$^1$H NMR (300 MHz) DMSO-$D_6$, 25° C.: $\delta$H (ppm) 8-7.5 (m, 5H, phthalic) 5-3.5 (m, overlap, 7H chitosan backbone).

Compound 3

N-bromosuccinimide (226.34 mmol) and TPP (226.34 mmol) were added to a solution of Compound 2 (7 g, 22.63 mmol of sugar unit) and NMP (700 mL) in an ice/water bath, and then the mixture was stirred at 80° C. for 8 h under nitrogen atmosphere. The dark brown reaction mixture was poured into EtOH (2 L), and the resulting precipitate was collected by centrifugation and filtration and then washed with EtOH, acetone-water, and then acetone. After drying under reduced pressure at 60° C., the bromo-deoxy derivative 3 was obtained as a dark brown powder.

$^1$H NMR (300 MHz) DMSO-$D_6$: $\delta$H (ppm) 8-7.5 (m, 5H, phthalic), 5.27 (1H, anomeric ring proton), 4.35-3.0 (m, overlap, 6H chitosan backbone).

Synthesis of 6-azido-N-phthaloyl chitosan (Compound 4) and Compound 5a

3

4

5a

Compound 4

Sodium Azide (8.73 g, 134.34 mmol) was added to a solution of Compound 3 (5 g, 13.43 mmol of sugar unit) in NMP (500 mL), and the mixture was stirred at 80° C. for 8 h under nitrogen atmosphere. The mixture was filtered through cotton to remove the salts and the filtrate was poured into EtOH (1.5 L). The resultant precipitate was collected by centrifugation and washed with EtOH, water, and then acetone. After drying under reduced pressure at 60° C., Compound 4 was obtained as a dark brown powder.

$^1$H NMR (300 MHz) DMSO-D$_6$: δH (ppm) 8-7.5 (m, 5H, phthalic), 5.27 (1H, anomeric ring proton), 4.35-2.90 (m, overlap, 6H chitosan backbone).

2,6-DAC (Compound 5a)

TPP (7.06 g, 26.92 mmol) was added to a solution of Compound 4 (3 g, 8.97 mmol of sugar unit) in NMP (200 mL), and the reaction solution was stirred at rt for 12 h under nitrogen atmosphere. The reaction mixture was then treated with aqueous hydrazine monohydrate (4 M, 200 mL) and stirred at 100° C. for 12 h. Following evaporation of the water, the suspended reaction mixture was poured into EtOH (2 L). The resultant precipitate was collected by centrifugation and washed with EtOH and acetone repeatedly to give Compound 5a as a brown powder.

$^1$H NMR (300 MHz) D$_2$O: δH (ppm) 5.2-4.9 (1H, anomeric ring proton), 4.35 (1H, C-4 proton), 4.1-2.5 (5H, C-2, 3, 5, 6).

Characterization

The synthesis of 2,6-DAC was tracked by $^1$H NMR and FTIR characterization. For Compound 2, the $^1$H NMR peaks at 7.5-8.0 ppm indicated the successful phthalic anhydride protection of the amino group on chitosan. After bromide substitution, the new FTIR signal at 657 cm$^{-1}$ (C—Br) indicated the successful grafting of Br at the 6-position of glucosamine. The substitution of bromide group by the azido group (Compound 4) was not trackable by $^1$H NMR. However, the azido group on Compound 4 was confirmed by the new FTIR signal at 2105 cm$^{-1}$ (N$_3$). For 2,6-DAC, the complete deprotection of the phthalic group was confirmed by disappearance of peaks at 7.5-8.0 ppm in the $^1$H NMR spectrum and the complete reduction of azido group was confirmed by the disappearance of the azido signal at 2105 cm$^{-1}$ and a further increase of the C—N bond signal at 1570 cm$^{-1}$ in the FTIR spectrum, indicating the conversion of C—N$_3$ to C—NH$_2$ at the 6-position of chitosan. The molecular weight of 2,6-DAC was 12 850 Da with polydispersity of 1.50 as calculated from GPC with pullulan as the standard.

Example 2

Synthesis of other amino-/imidazole/triazole chitosan derivatives (Compounds 5b-j)

To further explore the antimicrobial potential of chitosan, the 6'-position on glucosamine units of chitosan was modified into amine/imidazole/triazole groups. Therefore, various functional groups including imidazoles, polyamines and triazoles, were used to substitute the bromide group on Compound 3 (prepared in Example 1), resulting in a library of chitosan derivatives (Compounds 5b-j). As the primary amine is more reactive than secondary amine, the side-reaction of secondary amine may be avoided by controlling the amount of precursor amines added.

Synthesis of Compounds 5b-j

3

5b-j

-continued d e f g h i j

An amine selected from one of b-j (1.61 mmol) was added to a solution of Compound 3 (200 mg, 0.537 mmol of sugar unit, d.s. bromo 0.95) in NMP (5 mL), and the reaction solution was stirred at 80° C. for 12 h under nitrogen atmosphere. The reaction mixture was then treated with 4 M aqueous hydrazine monohydrate (5 mL) and stirred at 100° C. for 12 h. Then, the reaction mixture was cooled to rt and dialyzed (1 KDa cut-off dialysis membrane) against DI water for four days. Compounds 5b-j were obtained via lyophilization.

6-EG diamine chitosan (Compound 5b)

$^1$H NMR (300 MHz) D$_2$O: δH (ppm) 5.2-4.9 (1H, anomeric ring proton), 4.3-3.0 (18H, C-2, 3, 4, 5, 6, 7, 8, 9, 10).

6-Spermine Chitosan (Compound 5c)

$^1$H NMR (300 MHz) D$_2$O: δH (ppm) 5.2-4.9 (1H, anomeric ring proton), 4.3-2.5 (18H, C-2, 3, 4, 5, 6, 7, 9, 10, 13), 2.0 (4H, C-8), 1.7-1.6 (4H, C-11,12).

6-DET Chitosan (Compound 5d)

$^1$H NMR (300 MHz) D$_2$O: δH (ppm) 5.2-4.9 (1H, anomeric ring proton), 4.3-2.5 (14H, C-2, 3, 4, 5, 6, 7, 8, 9, 10).

6-EDA Chitosan (Compound 5e)

$^1$H NMR (300 MHz) D$_2$O: δH (ppm) 5.2-4.9 (1H, anomeric ring proton), 4.3-3.0 (10H, C-2, 3, 4, 5, 6, 7, 8).

6-Triamine Chitosan (Compound 5f)

$^1$H NMR (300 MHz) D$_2$O: δH (ppm) 5.2-4.9 (1H, anomeric ring proton), 4.3-2.5 (18H, C-2, 3, 4, 5, 6, 7, 8, 9, 10).

6-Aminopropyl Imidazole Chitosan (Compound 5g)

$^1$H NMR (300 MHz) D$_2$O: δH (ppm) 8.8 (1H, C-10), 7.6-7.3 (2H, C11, 12), 5.2-4.9 (1H, anomeric ring proton), 4.3-2.8 (10H, C-2, 3, 4, 5, 6, 7, 9), 2.5-2.0 (2H, C-8).

6-Diaminotriazole Chitosan (Compound 5h)

$^1$H NMR (300 MHz) D$_2$O: δH (ppm) 5.2-4.9 (1H, anomeric ring proton), 4.3-2.5 (6H, C-2, 3, 4, 5, 6).

6-Aminotriazole Chitosan (Compound 5i)

$^1$H NMR (300 MHz) D$_2$O: δH (ppm) 8.0 (1H, C-7), 7.6-7.3 (2H, C11, 12), 5.2-4.9 (1H, anomeric ring proton), 4.3-2.5 (6H, C-2, 3, 4, 5, 6).

6,3-Amino-4-Carboxamide Imidazole Chitosan (Compound 5j)

$^1$H NMR (300 MHz) D$_2$O: δH (ppm) 8.0-7.5 (1H, C-7), 7.6-7.3 (2H, C11, 12), 5.2-4.9 (1H, anomeric ring proton), 4.3-2.5 (6H, C-2, 3, 4, 5, 6).

Characterization

Compared with raw material chitosan, 6-triamine chitosan, 6-spermine Chitosan, 6-DET-chitosan, 6-EDA-chitosan, 6-EG-diamine chitosan showed alkyl group signal at 2.5-3.0 ppm. However, the peaks overlap with the sugar signal. For 6-Aminopropyl imidazole chitosan, 6-diamino triazole chitosan, 6-amino triazole chitosan and 6,3-amino-4-carboxamide imidazole chitosan, the synthesis was confirmed by the appearance of the imidazole group at 7.5-8.0 ppm.

Example 3

Colloidal Properties of 2,6-DAC Aggregation

Dynamic Light Scattering (DLS)

Figure 1:
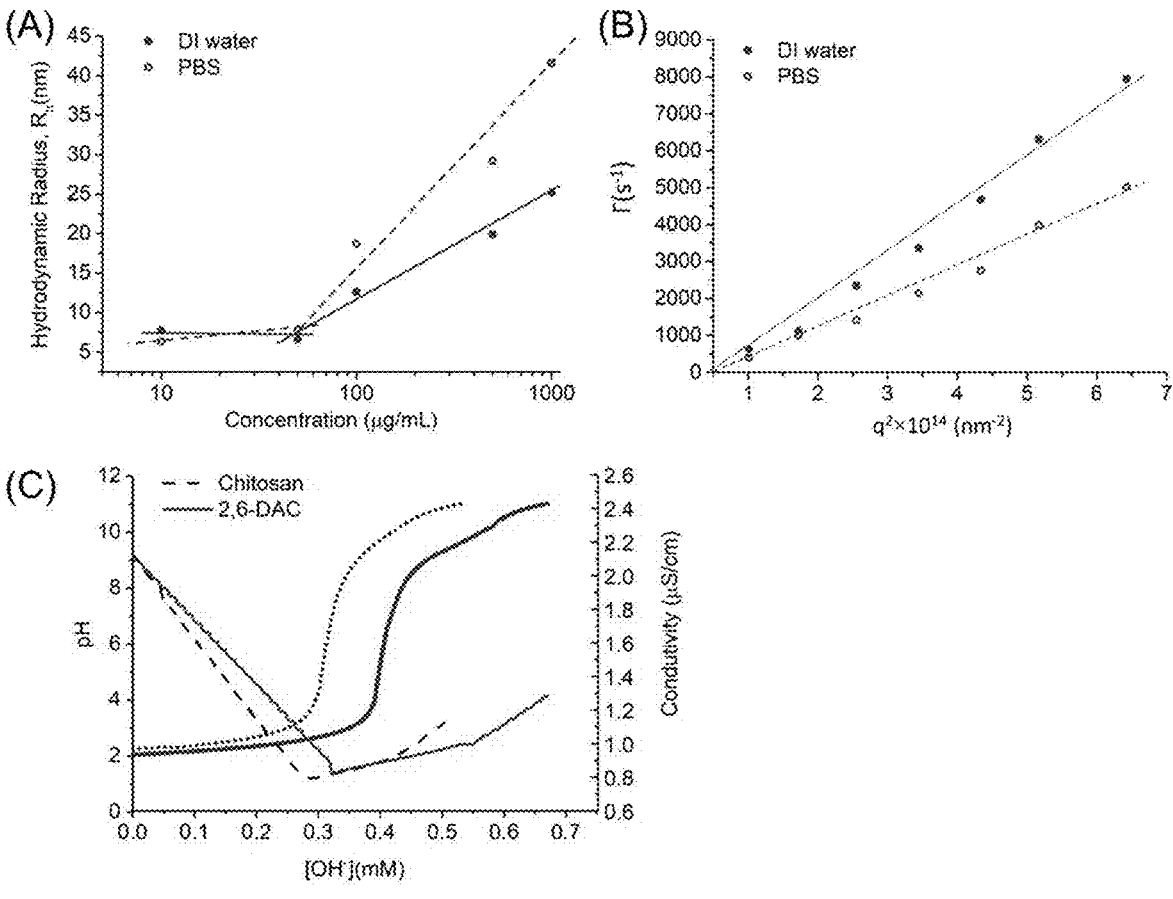
FIG. 1 depicts the colloidal properties of 2,6-DAC. (A) Critical aggregation concentration (CAC) determination by light scattering; (B) Dynamic light scattering (DLS) of 2,6-DAC in both DI water and PBS at 1 mg/mL: decay rate ($\Gamma$) versus wave vector ($q^2$) for 2,6-DAC at pH=7 in DI water and at pH=7.4 in PBS; and (C) pH potentiometric titration of chitosan compared with 2,6-DAC.

For the study of polymer aggregation, 10, 50, 100, 500 or 1000 µg of polymer was dissolved in 1 mL of deionized (DI) water (pH=7) or PBS (pH=7.4) and filtered against a 0.45 pm PES filter. The hydrodynamic radius (R$_h$) was calculated based on DLS measurements at 45°, 60°, 75°, 90°, 105°, 120°, 135°, and 150° scattering angles. The method of mathematical analysis of autocorrelation function based on light scattering follows the protocol published by Schillen et al. (K. Schillen, W. Brown & R. M. Johnsen, *Macromolecules* 1994, 27, 4825-4832).

pH-Potentiometric Titration pH titration was performed according to a published procedure with modification (Z. Hou et al., *ACS Appl. Mater. Interfaces* 2017, 9, 38288-38303). pH-potentiometric titrations of both chitosan and 2,6-DAC were performed with pH increasing from 2 to 12 to track the deprotonation process. A polymer solution of 10 mg/mL was prepared in 0.01 M HCl solution (with pH=12). The prepared solution (15 mL) was titrated with 10 µL droplets of 0.1 M NaOH until pH reached 12. The pH potentiometer used was an 809 Titrando Metrohm. The pH and conductivity of the solution in the beaker changed with the addition of NaOH and was plotted. The deprotonation process of the polysaccharides starts at point A where all the amino groups in polysaccharides are protonated, and finishes at point B, where all the amino groups in polysaccharide are deprotonated. The amount of protons accepted by chitosan and 2,6-DAC at pH=7 (point C) was calculated by the following equation:

The amount of protons accepted=amount of [OH$^{-1}$] at B—amount of [OH$^{-1}$] at C Results and Discussion Due to the hydrogen bonds between the polysaccharide backbones, 2,6-DAC can aggregate into nanoparticles in an aqueous environment at neutral pH. The critical aggregation concentration (CAC) of 2,6-DAC measured by light scattering was 50 µg/mL in both DI water and PBS (employed to mimic physiological conditions) (FIG. 1A). The 2,6-DAC polysaccharide chains aggregated into nanoparticles (FIG. 1B) with R$_h$ of 22.5 nm in DI water. Only aggregated nanoparticles without free polysaccharide chains were detected.

Chitosan aggregates are reported to have proton sponge effect due to the buffering capacity of primary amino groups (I. Richard et al., *Biomacromolecules* 2013, 14, 1732-1740). The proton sponge effect is responsible for antimicrobial efficacy of chitosan derivatives (Z. Hou et al., *ACS Appl. Mater. Interfaces* 2017, 9, 38288-38303). To compare the proton sponge effect of 2,6-DAC with native chitosan, 10 mg/mL of chitosan or 2,6-DAC underwent pH-potentiometric titration with pH increased from 2 to 12. From the pH-potentiometric titration curve (FIG. 10), more protons were accepted by 2,6-DAC (0.15 mM) as compared with native chitosan (0.053 mM) at neutral pH=7. Therefore, compared with native chitosan, the proton sponge effect of 2,6-DAC was more significant. The surface charge on 2,6-DAC nanoparticles were higher and upon contacting with anionic cytoplasm membrane of bacteria, the excess protons resulted in higher osmotic pressure which led to the rupture of the anionic membrane (A. Akinc et al., *J. Gene Med.* 2005, 7, 657-663).

Example 4

In Vitro Antimicrobial Efficacy and Cytotoxicity of Compounds 5a-5j

MIC Determination

MIC values were determined using a broth micro dilution method. Bacteria cells were grown overnight at 37° C. in MHB to a mid-log phase ($OD_{600}$ between 0.4-0.5 for each organism) and diluted in MHB to $10^5$ CFU/mL. The polymer selected from one of Compounds 5a-5j was dissolved in water to obtain a stock concentration of 10 mg/mL. The antibiotics selected from one of Ofloxacin, Levofloxacin, Azithromycin, Erythromycin, Meropenem, Imipenem, Ertapenem, Doripenem, Cephalothins, Cefoxitin, Ceftazidime, Ceftriaxone, Ramoplanin, Amoxicillin, Ampicillin, Carbenicillin, Novobiocin, Tobramycin, Trimethoprim, Ceftazidime, Chloramphenicol, Ciprofloxacin, Piperacillin, Polymyxin B, Amikacin, Colistin, Gramicidin and Tazobactam, was dissolved and prepared to stock concentrations according to CLSI guidelines. 50 µL of the $1-5\times10^5$ CFU/mL bacterial cultures (final concentration) was aliquoted into 96-well microtiter plates and mixed with 50 µL of two-fold dilutions of the polymer or antibiotics and incubated for 16-18 h at 37° C. with shaking at 200 rpm. Growth inhibition was determined by measuring the optical density at 600 nm ($OD_{600}$) of each well using a TECAN M200 microplate reader; the lowest concentration at which exhibited no bacterial growth is defined as the MIC.

Time Killing Assay

Bacteria cells were grown, diluted, and aliquoted into 96 well plates as described for the MIC assay above, and then mixed with 50 µL volume of medium containing 0.5× and 1×MIC of the polymer and/or antibiotics. The plates were sealed and incubated at 37° C. with shaking at 200 rpm.

At 0, 0.5, 1, 2, 3, 5, and 24 h post-inoculation, each well was thoroughly mixed with a multi-channel pipette and 20 µL of sample was removed, serially diluted in sterile PBS, plated on LB agar plates, and incubated at 37° C. for 12 h. Colonies were counted to determine the CFU/mL at each time point.

Mammalian Cell Biocompatibility Test Via MTT Cell Proliferation Assay

The mammalian cell biocompatibility test was done according to the published protocol using 3T3 cells (Z. Si et al., *Angew. Chem. Int. Ed.* 2020, 59, 6819-6826). In a 96-well plate, 3T3 cells were co-cultured for 24 h at 37° C. with polymer (100 µg/mL or 200 µg/mL) at initial cell density of $1\times10^5$ cells per well. At the end of the incubation period, the culture medium was removed, each well was washed with PBS followed by the addition of MTT solution, and the plate was incubated for 4 h at 37° C. The MTT medium was then removed, 100 µL of DMSO was added to each well, the plate was shaken at 100 rpm for 15 min and the absorbance at 570 nm was measured with plate reader (BIO-RAD Benchmark Plus, US).

Hemolytic Activity Test

Fresh rabbit blood (5 mL) was washed three times with sterilized PBS and diluted to a final concentration of 5% v/v. A series concentration of 2,6-DAC and Gramicidin control were incubated with the prepared erythrocyte suspension for 1 h with shaking in a 96-well plate. The supernatant (80 µL) was aliquoted to a new plate after centrifugation at 1000 g for 10 min. The absorbance at 540 nm was recorded by the TECAN microplate reader. 0.1% Triton X-100 that can lyse red blood cells completely was used as the positive control ($O_p$), and PBS was used as the negative control ($O_n$). The percentage of hemolysis was determined by the following equation:

$$Hemolysis\%=[(O_x-O_n)/(O_p-O_n)]\times100\%$$

Results and Discussion

Figure 2:
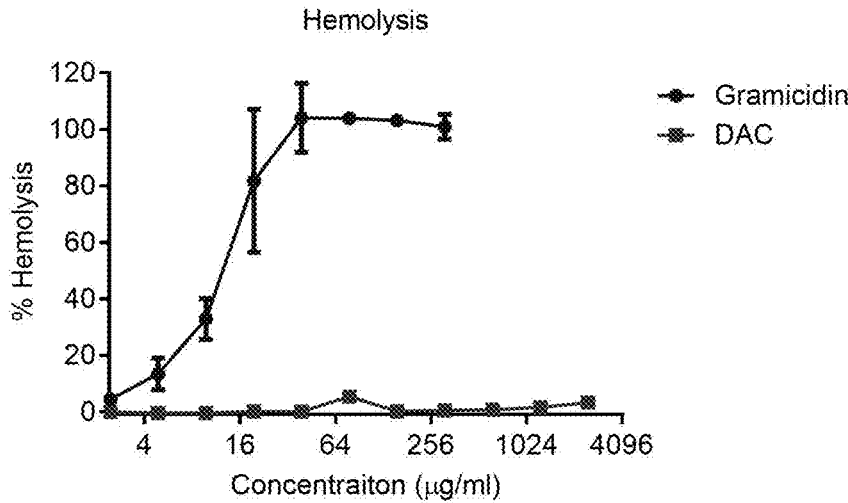
FIG. 2 depicts the hemolytic activity of 2,6-DAC and Gramicidin.

Table 1 summarizes the antimicrobial efficacy and cytotoxicity of 2,6-DAC. 2,6-DAC showed excellent broad-spectrum antimicrobial activity against both Gram-positive and Gram-negative bacteria with MICs of 8-32 µg/mL, including the clinically important MDR *A. baumannii* strains. The MICs against *S. aureus, E. coli* and *P. aeruginosa* are 16, 16-32 and 8 µg/mL respectively. Additionally, 2,6-DAC showed good biocompatibility as measured using the 3T3 fibroblast cells (Table 1). The 24 h cell viability with 200 µg/mL of 2,6-DAC was up to 94.25%. Furthermore, 2,6-DAC did not cause significant hemolysis at 2500 µg/ml while the control antimicrobial peptide (AMP) Gramicidin caused 100% hemolysis at 78 µg/mL (FIG. 2). The hemolytic result further supports the good biocompatibility of 2,6-DAC. However, the other chitosan derivatives grafted with imidazole or triazole groups showed either poor antimicrobial efficacy or low biocompatibility compared with 2,6-DAC (Table 2).

TABLE 1

Summary of in vitro biological properties of 2,6-DAC.

| | Minimum Inhibitory Concentration (MIC) (µg/mL) | | | | % Cell viability | |
|---|---|---|---|---|---|---|
| | Gram-negative bacteria | | Gram-positive bacteria | | | |
| Sample | *P. aeruginosa* | *E. coli* | *S. aureus* | MRSA | 100 µg/mL | 200 µg/mL |
| 2,6-Diamino Chitosan (2,6-DAC) | 8 | 16-32 | 16 | 16 | 98.63 | 94.25 |

TABLE 2

Summary of antimicrobial efficacy and cytotoxicity of 2,6-DAC and its derivatives.

| | | Minimum Inhibitory Concentration (MIC) (μg/mL) | | | | | | |
| | | Gram-negative bacteria | | | Gram-positive bacteria | | % Cell viability | |
| | | | | *A.* | | | 100 | 200 |
| Sample | | PAO1 | *E. coli* | *baumannii* | *S. aureus* | MRSA | μg/mL | μg/mL |
| | Chitosan | 512 | >512 | 512 | 512 | 512 | N.D. | N.D. |
| 5a | 2,6-Diamino Chitosan (2,6-DAC) | 8 | 16-32 | 8-32 | 16 | 16 | 98.63 | 94.25 |
| 5b | 6-Triamine Chitosan | 8 | 16 | N.D* | 16 | 16 | 5.8 | 5.7 |
| 5c | 6-Spermine Chitosan | 256 | 512 | N.D | 16 | 32 | 10.0 | 5.6 |
| 5d | 6-DET Chitosan | 8 | 256 | N.D | 16 | 64 | 87.9 | 23.3 |
| 5e | 6-EDA Chitosan | >512 | >512 | N.D | 32 | 32 | 85.1 | 70.2 |
| 5f | 6-EG Diamine Chitosan | 128 | 512 | N.D | 16 | 512 | 47.6 | 12.7 |
| 5g | 6-Aminopropyl imidazole Chitosan | >512 | 512 | N.D | >512 | >512 | 79.2 | 47.8 |
| 5h | 6-Diamino Triazole Chitosan | >512 | >512 | N.D | >512 | >512 | 89.4 | 45.8 |
| 5i | 6-Amino Triazole Chitosan | >512 | >512 | N.D | >512 | 512 | 83.1 | 79.0 |
| 5j | 6,3-Amino-4-Carboxamide Imidazole Chitosan | >512 | >512 | N.D | >512 | >512 | 91.2 | 52.1 |

*N.D: not determined

Compound 5b showed good and broad antimicrobial efficacy. Compounds 5c, 5e and 5f also showed selective antimicrobial activity against Gram-positive bacteria, but the biocompatibilities are poor. Compounds 5d, 5g, 5h, 5i and 5j showed good biocompatibility as measured using the 3T3 fibroblast cells (Table 2); however, their antimicrobial efficacy is low. Comparing the antibacterial activity with their cytotoxicity, only 2,6-DAC (Compound 5a) demonstrated excellent broad antimicrobial activity with good biocompatibility. Therefore, although polymers grafted with heterocyclic amino groups (C. Fang et al., *Polym. Chem.* 2019, 10, 209-218; and W. Tan et al., *Carbohydr. Polym.* 2016, 142, 1-7) have been reported to have antimicrobial efficacy, the simple amino group modification on 6-position (2,6-DAC) showed better antimicrobial efficacy compared with other derivatives grafted with imidazole or triazole groups. This balanced antimicrobial efficacy and biocompatibility of 2,6-DAC should be attributed to the introduction of amino groups which enhance the proton sponge effect and increase the hydrophilicity of chitosan. Compared with native chitosan, the proton sponge effect due to presence of amino groups is enhanced in 2,6-DAC, resulting in a higher cationic charge compared with native chitosan. The simple amino group in 2,6-DAC is also more hydrophilic compared with grafting of imidazole and triazole groups in other chitosan derivatives synthesized. The presence of the hydrophobic moieties reduces the biocompatibilities of the polymers. The more hydrophobic side groups also reduce the solubility of the chitosan derivatives or interrupt the hydrogen bond for aggregation; therefore, the antimicrobial potencies of the polymers are limited in solution.

Further, the antimicrobial efficacy of 2,6-DAC was evaluated against a panel of multidrug resistant (MDR) and clinically isolated bacteria (Table 3), including *L. monocytogenes*, *P. aeruginosa* BAA2797, and *K. pneumoniae*

Figure 3:
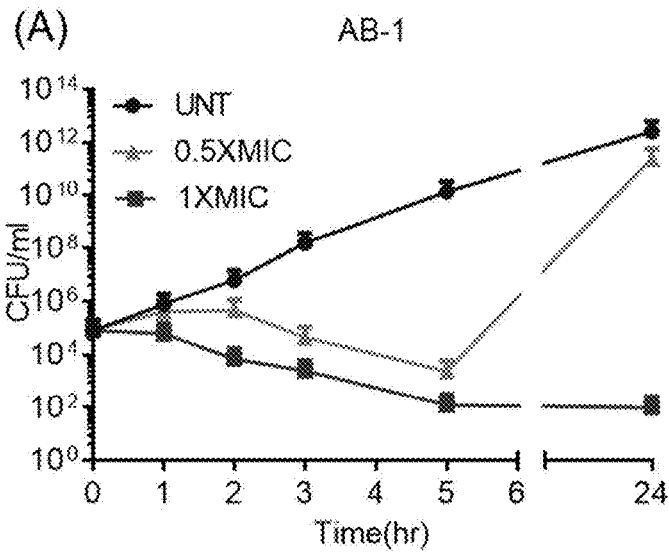
FIG. 3 depicts (A) time-killing kinetics of 2,6-DAC against *A. baumannii* AB-1 at 0.5×Minimum Inhibitory Concentration (MIC) and 1×MIC; and the killing kinetics of 2,6-DAC against (B)
Figure 3:
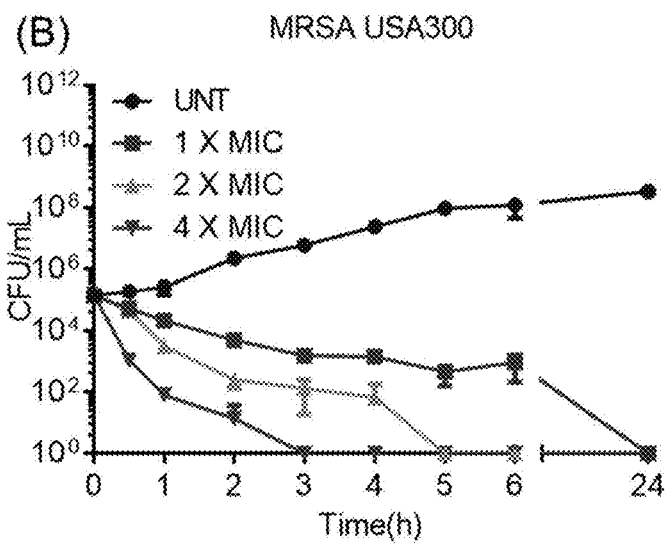
Figure 3:
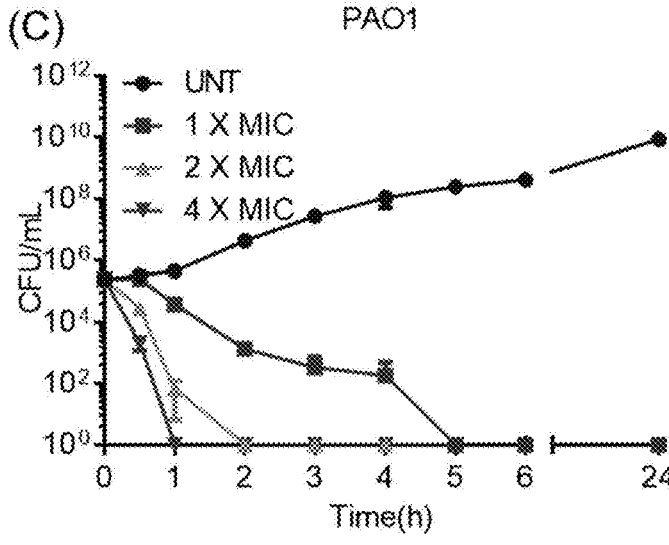

BAA2784. The MICs of 2,6-DAC against these bacteria tested were also excellent (MICs among 8-16 μg/mL). We further found that 2,6-DAC demonstrated good antibacterial activity with MICs in the range of 8 to 32 μg/mL against 3 *A. baumannii* strains (AB-1, BAA2803, 17,978, Table 3). The antimicrobial activity toward AB-1 was further confirmed by the time-kill assay (FIG. 3A), 2,6-DAC treated AB-1 rapidly stopped bacterial growth; the polymer displayed 3.5 $\log_{10}$ reduction at MIC level (32 μg/mL) in 24 h. The killing kinetics of 2,6-DAC against Gram-positive bacteria MRSA USA300 and Gram-negative bacteria *P. aeruginosa* PAO1 at 1×MIC, 2×MIC and 4×MIC showed that 2,6-DAC had fast killing kinetics against both Gram-positive bacteria MRSA USA300 (FIG. 3B) and Gram-negative bacteria *P. aeruginosa* PAO1 (FIG. 3C).

TABLE 3

Antimicrobial efficacy of 2,6-DAC against clinically relevant antibiotic-susceptible and MDR clinical isolates.

| | Minimum Inhibitory Concentration (MIC) (μg/mL) |
| Gram-negative bacteria | |
| *A. baumannii* AB-1 | 32 |
| *A. baumannii* BAA2803 | 8 |
| *A. baumannii* 17,978 | 16-32 |
| *P. aeruginosa* PAO1 | 8 |
| *P. aeruginosa* BAA2797 | 8 |
| *K. pneumoniae* 43,826 | 16 |
| *K. pneumoniae* BAA2784 | 16 |
| *E. coli* BAA2774 | 16 |
| Gram-positive bacteria | |
| *Listeria monocytogenes* | 16 |
| MRSA USA300 | 16 |

27

Example 5

Synergistic Study of 2,6-DAC with Antibiotics 2,6-DAC was screened as a potentiating agent for synergistic combinations with antibiotics against both *A. baumannii* AB-1 and MRSA USA300. Before the synergy tests, the MIC values of antibiotics were tested against MDR *A. baumannii* AB-1 and MRSA USA300 by following the MIC determination protocol in Example 4. Then, the synergy of 2,6-DAC with antibiotics was determined.

Measurement of Synergy

Synergy was measured by time killing assay and checkerboard assay. Time killing assay was performed by following the protocol in Example 4. Checkerboard susceptibility assays to measure combinations of antimicrobials were performed in MHB at 37° C. as previously described (K. R. V. Thappeta et al., *ACS Infect. Dis.* 2020, 6, 1228-1237; and Z. Si et al., *Angew. Chem. Int. Ed.* 2020, 59, 6819-6826). The fractional inhibitory concentration (FIC) indices were calculated according to the following formula:

$$FIC \text{ index} = FIC_A + FIC_B$$

Where $$FIC_A = \frac{MIC \text{ of drug } A \text{ in combination}}{MIC \text{ of drug } A \text{ alone}}$$

$$FIC_B = \frac{MIC \text{ of drug } B \text{ in combination}}{MIC \text{ of drug } B \text{ alone}}$$

Conservative interpretation of the FIC index has traditionally defined synergy as a FIC index ≤0.5, and the FIC index range from 0.5-1 as additive or partial synergy Also, the FIC index greater than 1 shows no synergy.

Antibiotic Accumulation Assay

The antibiotic accumulation assay was performed according to the published protocol (Z. Si et al., *Angew. Chem. Int. Ed.* 2020, 59, 6819-6826). $10^9$ CFU/mL log phase of *A. baumannii* AB-1 was incubated with rifampin alone (2 µg/mL) or rifampin (2 µg/mL)+2,6-DAC (8 µg/mL) with shaking at 37° C., 200 rpm. The cultured solution was quickly spun down 3 h after incubation and washed with ice-cold sterile PBS. The bacterial pellet was immediately snap-frozen in liquid nitrogen after washing three times.

The frozen pellets were gradually thawed on ice followed by the addition of 1 mL 80% (v/v) methanol in water and mixed for 30 s. The dissolved samples were sonicated in an ice water bath for 60 min at 100% power. The samples were subsequently centrifuged at 10,000 g for 10 min at 4° C. The supernatant (800 µL) was collected for each sample, diluted with 2 mL of ultrapure water in a falcon tube, and stored at −80° C. before further processing. The frozen samples were lyophilized. The obtained powder was dissolved in 500 µL of 50% (v/v) aqueous methanol and was subjected to LC-MS studies.

Efflux Inhibition Assay

Log-phase *A. baumannii* AB-1 were centrifuged and washed twice with sterilized PBS. $10^8$ CFU/mL bacterial suspension was incubated with ethidium bromide (16 µg/mL) to achieve the maximum accumulation. The free ethidium bromide was removed by centrifugation at 3000 g for 5 min. The recovered bacterial pellet was resuspended in fresh PBS and treated with 2,6-DAC or CCCP at the desired concentration. Glucose was added to 0.4% concentration. Fluorescence was recorded using the TECAN fluorescence spectrometer at 37° C. under 530 nm excitation and 585 nm emission.

Results and Discussion

The MIC values of antibiotics were tested against MDR *A. baumannii* AB-1 (Table 4) and MRSA USA300 (Table 5). As shown in Table 4, 2,6-DAC displayed potent synergy with antibiotics that function as protein synthesis inhibitors (tobramycin and amikacin) against MDR pathogen AB-1. Both tobramycin and amikacin had FIC indices as low as 0.265 in combination with 2,6-DAC. Combining 2,6-DAC at a combination concentration of 8 and 16 µg/mL, the MICs of both amikacin and tobramycin were reduced greatly from >128 µg/mL to 1-2 µg/mL. Furthermore, 2,6-DAC demonstrated synergy with novobiocin (Table 4), a DNA gyrase inhibitor, with FIC as low as 0.312. Combining with 2,6-DAC at a concentration of 8 µg/mL, the sensitivity to novobiocin was restored, as the antibiotic MIC reduced from 8 µg/mL to 0.5 µg/mL. Additionally, 2,6-DAC also displayed synergy with tazobactam (FIC=0.5), a β-lactamase inhibitor (Table 4). Therefore, 2,6-DAC showed synergistic activity with various kinds of antibiotics including amikacin, tobramycin, novobiocin, rifampicin and tazobactam. However, 2,6-DAC only had partial synergies (0.5<FIC<1) with other antibiotics against MDR AB-1 (Table 6). For MRSA USA300, 2,6-DAC also showed synergy with carbenicillin (FIC=0.5), novobiocin (FIC=0.312) and tobramycin (FIC=0.312) (Table 5). For both Gram-positive and Gram-negative bacteria tested, novobiocin combined with 2,6-DAC showed the best bactericidal efficacy among the antibiotics tested.

TABLE 4

Summary of synergistic study of 2,6-DAC with various antibiotics against *A. baumannii* AB-1.

| Antibiotics | Antimicrobial mechanisms | MIC µg/mL | | | |
| | | Without 2,6-DAC | Antibiotic in combination (µg/mL) | 2,6-DAC in combination (µg/mL) | FIC |
| --- | --- | --- | --- | --- | --- |
| Amikacin | Protein synthesis inhibitor | >128 | 2 | 8 | 0.265 |
| Tobramycin | Protein synthesis inhibitor | >128 | 2 | 8 | 0.265 |
| Novobiocin | DNA gyrase inhibitor | 8 | 0.5 | 8 | 0.312 |
| Tazobactam | β-lactamase inhibitor | 64 | 16 | 8 | 0.5 |

TABLE 5

FIC indices of antibiotics in combination with 2,6-DAC against MRSA USA300.

| Antibiotics | Antimicrobial mechanisms | MIC μg/mL Without 2,6-DAC | Antibiotic in combination (μg/mL) | 2,6-DAC in combination (μg/mL) | FIC |
|---|---|---|---|---|---|
| Carbenicillin | β-lactamase inhibitor | 8 | 2 | 4 | 0.5 |
| Tobramycin | Protein synthesis inhibitor | 1 | 0.25 | 1 | 0.312 |
| Novobiocin | DNA gyrase inhibitor | 0.125 | 0.03125 | 1 | 0.312 |

TABLE 6

FIC indices of antibiotics in combination with 2,6-DAC against *A. baumannii* AB-1 (MDR) with partial synergistic effect (0.5 < FIC < 1).

| Antibiotics | Antimicrobial mechanisms | MIC μg/mL Without 2,6-DAC | +32 μg/mL 2,6-DAC | +16 μg/mL 2,6-DAC | FIC |
|---|---|---|---|---|---|
| Ofloxacin | DNA gyrase inhibitor | 8 | 4 | 8 | 1 |
| Levofloxacin | DNA gyrase inhibitor | 4 | ≤1 | 2 | 1 |
| Azithromycin | Protein synthesis inhibitor | 128 | 1 | 64 | 1 |
| Erythromycin | Protein synthesis inhibitor | >128 | 4 | 64 | 1 |
| Meropenem | Cell wall synthesis inhibitor | 64 | 1 | 4 | 0.5625 |
| Imipenem | Cell wall synthesis inhibitor | 64 | 1 | 8 | 0.625 |
| Ertapenem | Cell wall synthesis inhibitor | >128 | 2 | 4 | 0.53125 |
| Doripenem | Cell wall synthesis inhibitor | 32 | ≤2 | 4 | 0.625 |
| Cephalothins | Cell wall synthesis inhibitor | >128 | 2 | 128 | 1 |
| Cefoxitin | Cell wall synthesis inhibitor | >128 | 8 | 128 | 1 |
| Ceftazidime | Cell wall synthesis inhibitor | >128 | 2 | 128 | 1 |
| Ceftriaxone | Cell wall synthesis inhibitor | >128 | 2 | 128 | 1 |
| Ramoplanin | Cell wall synthesis inhibitor | >128 | 2 | 128 | 1 |
| Amoxicillin | Cell wall synthesis inhibitor | >128 | 16 | 128 | 1 |

TABLE 7

FIC indices of antibiotics in combination with 2,6-DAC against MRSA USA300.

| Antibiotics | MIC alone (μg/mL) | Antibiotic in combination (μg/mL) | 2,6-DAC in combination (μg/mL) | FIC |
|---|---|---|---|---|
| Ampicillin | 4 | 2 | 0.25 | 0.75 |
| Carbenicillin | 8 | 2 | 0.5 | 0.28125 |
| Meropenem | 1 | 0.5 | 0.25 | 0.51 |
| Novobiocin | 0.125 | 0.03125 | 0.5 | 0.28 |
| Tobramycin | 1 | 0.25 | 1 | 0.31 |
| Trimethoprim | 1 | | no synergy | |
| Ceftazidime | 16 | | no synergy | |
| Chloramphenicol | 4 | | no synergy | |
| Ciprofloxacin | 8 | | no synergy | |
| Piperacillin | 4 | | no synergy | |
| Polymyxin B | 32 | | no synergy | |
| Amikacin | 1.5625 | | no synergy | |
| Trimethoprim | 1 | | no synergy | |
| Ceftriaxone | 16 | | no synergy | |
| Colistin | 50 | | no synergy | |

Moreover, synergistic effects of 2,6-DAC with antibiotics against AB-1 were demonstrated by time-killing curves (FIG. 4). At sub-inhibitory concentration, both 2,6-DAC and the antibiotics tested (novobiocin, amikacin, tobramycin and tazobactam) showed no killing of bacteria after 24 h. Combinations of sub-inhibitory concentrations of 2,6-DAC (0.25×MIC) with sub-inhibitory concentrations of novobiocin (0.125 to 0.25×MIC) (FIG. 4A) were found to be synergistic and achieved 4 $\log_{10}$ orders of bacteria killing. Similarly, combination of 2,6-DAC (0.5×MIC) with tazobactam (0.06×MIC) and amikacin (0.002×MIC) (FIG. 4B-C) demonstrated synergistic effects with 4 $\log_{10}$ bactericidal efficacy. However, the overall bactericidal efficacy of tobramycin (0.002×MIC) and 2,6-DAC (0.5×MIC) combination (FIG. 4D) was poor with 2 $\log_{10}$ reduction against AB-1. It is worth noticing that the 2,6-DAC+novobiocin and 2,6-DAC+tobramycin combinations did not cause toxicity against mammalian NIH 3T3 cells; the cell viability of both combination groups was more than 95% (FIG. 5). The synergy between 2,6-DAC and antibiotics seems dependent on the antimicrobial mechanisms of the antibiotics. 2,6-

DAC showed a better synergistic effect with DNA gyrase inhibitor (novobiocin), protein synthesis inhibitor (amikacin and tobramycin) and β-lactamase inhibitor (tazobactam).

route did not cause any decrease of body weight in 7 days (FIG. 7B), reflecting a good biocompatibility of 2,6-DAC by oral administration.

TABLE 8

In vivo toxicity of 2,6-DAC, the effect on liver and kidney functions as well as balance of electrolytes in the blood.

| | ALT*(UI$^{-1}$) | AST** (UI$^{-1}$) | TBIL*** ($\mu$mol$^{-1}$) | Creatinine ($\mu$mol$^{-1}$) | Urea nitrogen (mmol$^{-1}$) | Potassium (mmol$^{-1}$) | Sodium (mmol$^{-1}$) |
|---|---|---|---|---|---|---|---|
| BUNT | 44.00 ± 7.07 | 99.80 ± 23.52 | 3.72 ± 1.10 | 53.20 ± 27.67 | 8.27 ± 0.72 | 5.46 ± 0.22 | 147.2 ± 5.45 |
| 1 day | 55.80 ± 9.88 | 106.8 ± 17.02 | 3.60 ± 1.17 | 42.40 ± 14.47 | 7.58 ± 0.76 | 5.31 ± 0.24 | 144.2 ± 2.05 |
| 7 days | 54.20 ± 24.08 | 92.80 ± 24.90 | 4.27 ± 0.81 | 57.40 ± 18.39 | 10.65 ± 0.96 | 5.79 ± 1.78 | 143.2 ± 1.10 |

$^a$UNT: Untreated Control;
*ALT: Alanine transaminase;
**AST: Aspartate aminotransferase;
***TBIL: Total Bilirubin.

The cell wall synthesis inhibitor only showed partial synergy with 2,6-DAC (Table 6).

The drug accumulation study showed that the antibiotic concentration of combination of rifampicin and 2,6-DAC inside bacteria was significantly higher than the antibiotic alone (FIG. 6A), indicating that the antimicrobial mechanism of polymer/antibiotic combination is that 2,6-DAC increases the membrane permeability of bacteria to let more antibiotics reach its target inside bacteria. Moreover, the negative result of 2,6-DAC on the efflux inhibition indicated that the potentiating effect of 2,6-DAC does not involve in the efflux inhibition (FIG. 6B).

Example 6

In Vivo Toxicity and Antimicrobial Efficacy of 2,6-DAC

In Vivo Oral and Intraperitoneal Toxicity Determination A single high dose of 100 mg/kg of 2,6-DAC was administered by the oral route for Balb/c mice. The body weight of the mice was determined. The mice were observed in detail for any indications of toxicity effect within the first 6 h after administration, and daily further for a period of 7 days. All the animals were weighed and visual observations for mortality, behavioral pattern, changes in physical appearance, injury, pain and signs of illness were conducted daily during the period.

Further, a single dosage of 25 mg/kg 2,6-DAC was injected intraperitoneally. The biomarkers were determined before treatment (Day 0), and Day 1 and Day 7 after administration. The biomarkers of Day 0 were the untreated controls. The animal experiments were carried out in accordance to the Code of Practice for the Institutional Care and Use of Animals for Scientific Purposes and were approved by the Ethics Committee of Ningbo University.
Results and Discussion The in vivo toxicity of 2,6-DAC was measured by intraperitoneal injection at 25 mg/kg and by oral delivery at 100 mg/kg. The systemic toxicity and oral toxicity were quantified by monitoring liver and kidney biomarkers and body weight. A single dosage of 25 mg/kg 2,6-DAC by intraperitoneal injection did not cause a significant change in the biomarkers associated with kidney and liver functions (FIG. 7A) indicating it neither caused any liver and kidney toxicity nor influenced the blood electrolytes (Table 8). More interesting, a single dosage of 100 mg/kg 2,6-DAC through oral Example 7

In Vivo Test of Synergy of 2,6-DAC with Antibiotics

The synergistic activity of 2,6-DAC with novobiocin and rifampicin was proven by the in vivo intraperitoneal or lung infection models.
Intraperitoneal Infection Model Bacterial cultures of MDR A. baumannii (AB-1) were prepared and used to infect 8-week-old female BALB/c mice. $10^6$ CFU/mL of AB-1 (300 μL) was injected into the intraperitoneal cavity to introduce the infection. After 2 h of infection, specific dosage of antibiotic (novobiocin or rifampicin, 10 mg/kg), 2,6-DAC (25 mg/kg) or the combination of antibiotic (novobiocin or rifampicin, 10 mg/kg) and 2,6-DAC (25 mg/kg) were injected into the intraperitoneal cavity. PBS was used as a control. Mice euthanasian at the indicated time points (18 h) was achieved by $CO_2$ asphyxiation followed by cervical dislocation. The intraperitoneal fluid, kidney, spleen and liver were recovered, and counted for bacteria concentration. For histopathological analysis, the kidney, spleen and liver were fixed in 10% neutral buffered formalin and embedded in paraffin. The paraffin-embedded sections were stained with H&E. The animal studies were carried out in accordance to protocol (A20029) approved by the NTU Institutional Animal Care and Use Committee (NTU-IACUC).
Lung Infection Model The mice were immunosuppressed following the published protocol before infection (T. F. Durand-Réville et al., Nat. Microbiol. 2017, 2, 17104). Bacterial cultures of MDR . baumannii (AB-1) were prepared and used to infect 8-week-old female BALB/c mice. $10^8$ CFU/mL of AB-1 (30 μL) was inhaled by the mouse to introduce the infection via the intranasal route. After 2 h of infection, a specific dosage of antibiotic (novobiocin or rifampicin, 10 mg/kg), 2,6-DAC (25 mg/kg) or the combination of antibiotic (novobiocin or rifampicin, 10 mg/kg) and 2,6-DAC (25 mg/kg) were administrated through the intranasal route for 2,6-DAC and through the intraperitoneal route for antibiotic. Mice euthanasian at indicated time points (24 h) was achieved by $CO_2$ asphyxiation followed by cervical dislocation. For histopathological analysis, the lung was fixed in 10% neutral buffered formalin and embedded in paraffin. The paraffin-embedded sections were stained with H&E. The lung was recovered and counted for bacteria concentration. The animal studies were carried out in accordance to protocol (A19001) approved by the NTU Institutional Animal Care and Use Committee (NTU-IACUC).

Results and Discussion

The in vivo synergy between 2,6-DAC and novobiocin or rifampicin against MDR *A. baumannii* (AB-1) was evaluated in both intraperitoneal and lung infection models. In the intraperitoneal model, bacteria were firstly introduced by intraperitoneal injection, followed by injection of drug treatment after 2 h. FIGS. 7C and 8 show that 2,6-DAC (25 mg/kg) or novobiocin (10 mg/kg) alone was ineffective in both intraperitoneal fluid and distal organs such as liver, kidney and spleen. However, the combination of 2,6-DAC (25 mg/kg) and novobiocin (10 mg/kg) led to 99.99% (4.1 $\log_{10}$) eradiation of bacteria in the intraperitoneal cavity. Moreover, reduction of bacteria was also observed in distal organs, including kidneys (99.3%, 2.2 $\log_{10}$, FIG. 8A), liver (99.6%, 2.5 $\log_{10}$, FIG. 8B) and spleen (99.7%, 2.6 $\log_{10}$, FIG. 8C). Histological analysis of liver, spleen and kidney for infection control, 2,6-DAC alone, novobiocin alone and their combination was also performed with the normal mice as the comparison group. The individual treatment groups by both 2,6-DAC and novobiocin did not improve the tissue appearance compared to the infection control group; congestion of central vein and infiltration of inflammatory cells, immune cell apoptosis and their exchange with blood cells, hyperaemic interstitial capillaries and tubular necrosis were observed in liver, spleen and kidney, respectively (FIG. 9). However, the combination treatment groups significantly alleviated these tissue abnormalities associated with bacterial infections (R. Lei et al., *ACS Nano* 2018, 12, 5284-5296; Z. Ren et al., *Sci. Rep.* 2020, 10, 5109; and G. Silva-Santana et al., *J. Clin. Exp. Pathol.* 2016, 6, 283), which are closer to the tissue appearance from normal mice (FIG. 9).

Furthermore, the proof of efficacy of combination treatment was demonstrated in a neutropenic lung infection model. Rifampicin (10 mg/kg) alone had around 1.6 $\log_{10}$ reduction on the lung bacteria while 2,6-DAC (25 mg/kg) did not have any protective effect (FIG. 7D). However, the combination treatment (rifampicin+2,6-DAC) further improved the rifampicin efficacy from around 1.6 $\log_{10}$ to 2.5 $\log_{10}$ of bacteria reduction (FIG. 6D). Similarly, histological analysis of lung for infection control, 2,6-DAC alone, rifampicin alone, and their combination was also performed with the normal mice as the comparison group. The tissues of 2,6-DAC and infection control groups showed remarkable effusion in the alveolus and thickened respiratory membranes in the lungs (FIG. 10). In contrast, the tissues from rifampicin-treated group showed partially alleviated these abnormalities associated with bacterial infections (J. Mwangi et al., *Proc. Natl. Acad. Sci. U.S.A.* 2019, 116, 26516-26522), while the tissues from the combination treatment by 2,6-DAC and rifampicin remarkably eliminated these abnormalities, which are closer to the tissue appearance from normal mice (FIG. 10).

The invention claimed is:

1. A pharmaceutical composition comprising a compound of formula I or a pharmaceutically acceptable salt or solvate thereof, an antibiotic or a pharmaceutically acceptable salt or solvate thereof, and a pharmaceutically acceptable carrier, where the compound of formula I is:

where:

the sum of m and n is 1 and each of m and n is from 0.1 to 0.9;

each $R_1$ is selected from $NH_2$ and $NH$—$(CH_2)_a$—X;

a is 2 to 3;

X is selected from O—$(CH_2)_2$—O—$(CH_2)_2$—$NH_2$, $NH_2$, $NH$—$(CH_2)_b$—Y and $N((CH_2)_c$—$NH_2)_2$;

b and c are each independently selected from 2 to 4,

Y is selected from $NH_2$ or $NH$—$(CH_2)_d$—$NH_2$, d is selected from 2 to 4, and wherein the antibiotic is selected from the group consisting of ampicillin, carbenicillin, meropenem, novobiocin, tobramycin, amikacin, tazobactam, and rifampicin.

2. The pharmaceutical composition according to claim 1, wherein the pharmaceutical composition further comprises one or more pharmaceutically acceptable excipients and adjuvants.

3. The pharmaceutical composition of claim 1, wherein m is 0.8 and n is 0.2.

4. The pharmaceutical composition of claim 1, wherein the compound of formula I, or a pharmaceutically acceptable salt or solvate thereof, is selected from the list:

-continued

; and

.

;

;

; and

.

5. The pharmaceutical composition of claim 1 wherein the compound of formula I or a pharmaceutically acceptable salt or solvate thereof is:

.

6. The pharmaceutical composition of claim 1, wherein the compound of formula I has a number-average molecular weight of from 7,000 to 15,000 Da.

7. The pharmaceutical composition of claim 6, wherein the compound of formula I has a number-average molecular weight of about 12,850 Da.

8. The pharmaceutical composition of claim 1, wherein the compound of formula I has a polydispersity of from 1.0 to 2.0, as measured using gel permeation chromatography.

9. A kit of parts comprising:

(a) a pharmaceutical composition comprising a compound of formula I or a pharmaceutically acceptable salt or solvate thereof, and a pharmaceutically acceptable carrier, where the compound of formula I is:

where:

the sum of m and n is 1 and each of m and n is from 0.1 to 0.9;

each $R_1$ is selected from $NH_2$ and $NH$—$(CH_2)_a$—X a is 2 to 3;

X is selected from O—$(CH_2)_2$—O—$(CH_2)_2$—$NH_2$, $NH_2$, $NH$—$(CH_2)_b$—Y and $N((CH_2)_c$—$NH_2)_2$ b and c are each independently selected from 2 to 4, Y is selected from $NH_2$ or $NH$—$(CH_2)_d$—$NH_2$, d is selected from 2 to 4;

and (b) a pharmaceutical composition comprising an antibiotic or a pharmaceutically acceptable salt or solvate thereof, and a pharmaceutically acceptable carrier, wherein the antibiotic is selected from the group consisting of ampicillin, carbenicillin, meropenem, novobiocin, tobramycin, amikacin, tazobactam, and rifampicin.

10. The kit of parts according to claim 9, wherein each of the pharmaceutical compositions further comprises one or more pharmaceutically acceptable excipients and adjuvants.

11. The kit of parts of claim 9, wherein m is 0.8 and n is 0.2.

12. The kit of parts of claim 9, wherein the compound of formula I, or a pharmaceutically acceptable salt or solvate thereof, is selected from the list:

;

-continued

13. The kit of parts of claim 9, wherein the compound of formula I or a pharmaceutically acceptable salt or solvate thereof is:

14. The kit of parts of claim 9, wherein the compound of formula I has a number-average molecular weight of from 7,000 to 15,000 Da.

15. The kit of parts of claim 14, wherein the compound of formula I has a number-average molecular weight of about 12,850 Da.

16. The kit of parts of claim 9, wherein the compound of formula I has a polydispersity of from 1.0 to 2.0, as measured using gel permeation chromatography.

17. A method of treating a microbial infection in a subject, the method comprising administering a pharmaceutically effective amount of a compound of formula I or a pharmaceutically acceptable salt or solvate thereof, and an antibiotic or a pharmaceutically acceptable salt or solvate thereof, wherein the compound of formula I is administered sequentially, simultaneously or concomitantly with the antibiotic, and wherein the compound of formula I is:

where:

the sum of m and n is 1 and each of m and n is from 0.1 to 0.9;

each $R_1$ is selected from $NH_2$ and $NH$—$(CH_2)_a$—X a is 2 to 3;

X is selected from O—$(CH_2)_2$—O—$(CH_2)_2$—$NH_2$, $NH_2$ and $NH$—$(CH_2)_b$—Y, $N((CH_2)_c$—$NH_2)_2$;

b and c are each independently selected from 2 to 4,

Y is selected from $NH_2$ or $NH$—$(CH_2)_d$—$NH_2$, d is selected from 2 to 4, and wherein the antibiotic is selected from the group consisting of ampicillin, carbenicillin, meropenem, novobiocin, tobramycin, amikacin, tazobactam, and rifampicin.

* * * * *